US010460835B2

(12) United States Patent
Semen et al.

(10) Patent No.: US 10,460,835 B2
(45) Date of Patent: Oct. 29, 2019

(54) SYSTEM AND METHOD FOR MEDICAL DEVICE IDENTIFIER

(71) Applicant: ResMed Limited, Bella Vista (AU)

(72) Inventors: Timothy Semen, Ambler, PA (US); Elliott Murray, Surry Hills (AU)

(73) Assignee: ResMed Inc., San Diego, CA (US)

(*) Notice: Subject to any disclaimer, the term of this patent is extended or adjusted under 35 U.S.C. 154(b) by 736 days.

(21) Appl. No.: 14/432,825

(22) PCT Filed: Oct. 1, 2013

(86) PCT No.: PCT/AU2013/001124
§ 371 (c)(1),
(2) Date: Apr. 1, 2015

(87) PCT Pub. No.: WO2014/053010
PCT Pub. Date: Apr. 10, 2014

(65) Prior Publication Data
US 2015/0199479 A1 Jul. 16, 2015

Related U.S. Application Data

(60) Provisional application No. 61/708,437, filed on Oct. 1, 2012.

(51) Int. Cl.
G06Q 50/00 (2012.01)
G16H 10/60 (2018.01)
(Continued)

(52) U.S. Cl.
CPC ........... *G16H 10/60* (2018.01); *G06F 16/245* (2019.01)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS 4,782,832 A   11/1988 Trimble et al.
4,944,310 A   7/1990 Sullivan
(Continued)

FOREIGN PATENT DOCUMENTS

WO   19980004310 A1   2/1998
WO   19980034665 A1   8/1998
(Continued)

OTHER PUBLICATIONS

International Preliminary Report on Patentability for Application No. PCT/AU2013/001124 dated Apr. 7, 2015.
(Continued)

*Primary Examiner* — Victoria P Augustine
*Assistant Examiner* — Chad A Newton
(74) *Attorney, Agent, or Firm* — Botos Churchill IP Law LLP

(57) ABSTRACT

A method and system assists in management of data associated with a home medical equipment (HME) device provided to a patient. An HME identifier may be received by a physician terminal or an HME provider terminal. In an example, an HME identifier may be stored, encoded, engraved or otherwise applied to a component of an HME device such as a removable storage medium (e.g., an SD card). A records management system may then be searched for a patient record associated with the HME device identifier based on retrieval of the identifier from the component. If a patient record is found, the identity of the patient may be verified. Optionally, if no such patient record is found, then a new patient record associated with the HME identifier may be created.

14 Claims, 36 Drawing Sheets

(51) Int. Cl.
*G06F 16/245* (2019.01)
*G06Q 10/00* (2012.01)

(58) Field of Classification Search
CPC ........ G06F 19/30; G06F 19/32; G06F 19/321;
G06F 19/324; G06F 19/325; G06F
19/326; G06F 19/328; G06F 19/34; G06F
19/3418; G06F 19/3456; G06F 19/3462;
G06F 19/3468; G06F 19/3475; G06F
19/3481; G06F 19/36; A61N 1/08; G16H
10/00; G16H 10/20; G16H 10/40; G16H
10/60; G16H 10/65; G16H 15/00; G16H
20/00; G16H 20/10; G16H 20/13; G16H
20/17; G16H 20/30; G16H 20/40; G16H
20/60; G16H 20/70; G16H 20/90; G16H
30/00; G16H 30/20; G16H 30/40; G16H
40/00; G16H 40/20; G16H 40/40; G16H
40/60; G16H 40/63; G16H 40/67; G16H
50/00; G16H 50/20; G16H 50/30; G16H
50/50; G16H 50/70; G16H 50/80; G16H
70/00; G16H 70/20; G16H 70/14; G16H
70/60; G16H 80/00
See application file for complete search history.

(56) References Cited

U.S. PATENT DOCUMENTS

| | | | |
|---|---|---|---|
| 6,532,959 B1 | 3/2003 | Berthon-Jones | |
| 6,581,594 B1 | 6/2003 | Drew et al. | |
| 7,835,926 B1* | 11/2010 | Naidoo | A61B 5/0002 |
| | | | 705/2 |
| 2004/0172302 A1* | 9/2004 | Martucci | A61B 5/0002 |
| | | | 705/2 |
| 2009/0044808 A1 | 2/2009 | Guney et al. | |
| 2009/0050156 A1 | 2/2009 | Ng et al. | |
| 2009/0192648 A1 | 7/2009 | Namineni et al. | |
| 2010/0000534 A1 | 1/2010 | Kooij et al. | |
| 2012/0030229 A1* | 2/2012 | Ji | G06F 19/322 |
| | | | 707/769 |

FOREIGN PATENT DOCUMENTS

| | | |
|---|---|---|
| WO | 00078381 A1 | 12/2000 |
| WO | 2004073778 A1 | 9/2004 |
| WO | 2005063328 A1 | 7/2005 |
| WO | 2006035351 A2 | 4/2006 |
| WO | 20060074513 A1 | 7/2006 |
| WO | 2006130903 A1 | 12/2006 |
| WO | 2009052560 A1 | 4/2009 |
| WO | 20100135785 A1 | 12/2010 |
| WO | 2011028261 A2 | 3/2011 |

OTHER PUBLICATIONS

International Search Report for Application No. PCT/AU2013/001124 dated Jan. 15, 2014.
Partial IInternational Search for Application No. PCT/AU2013/001124 dated Dec. 3, 2013.
Written Opinion for Application No. PCT/AU2013/001124 dated Jan. 15, 2014.

* cited by examiner

Fig. 10

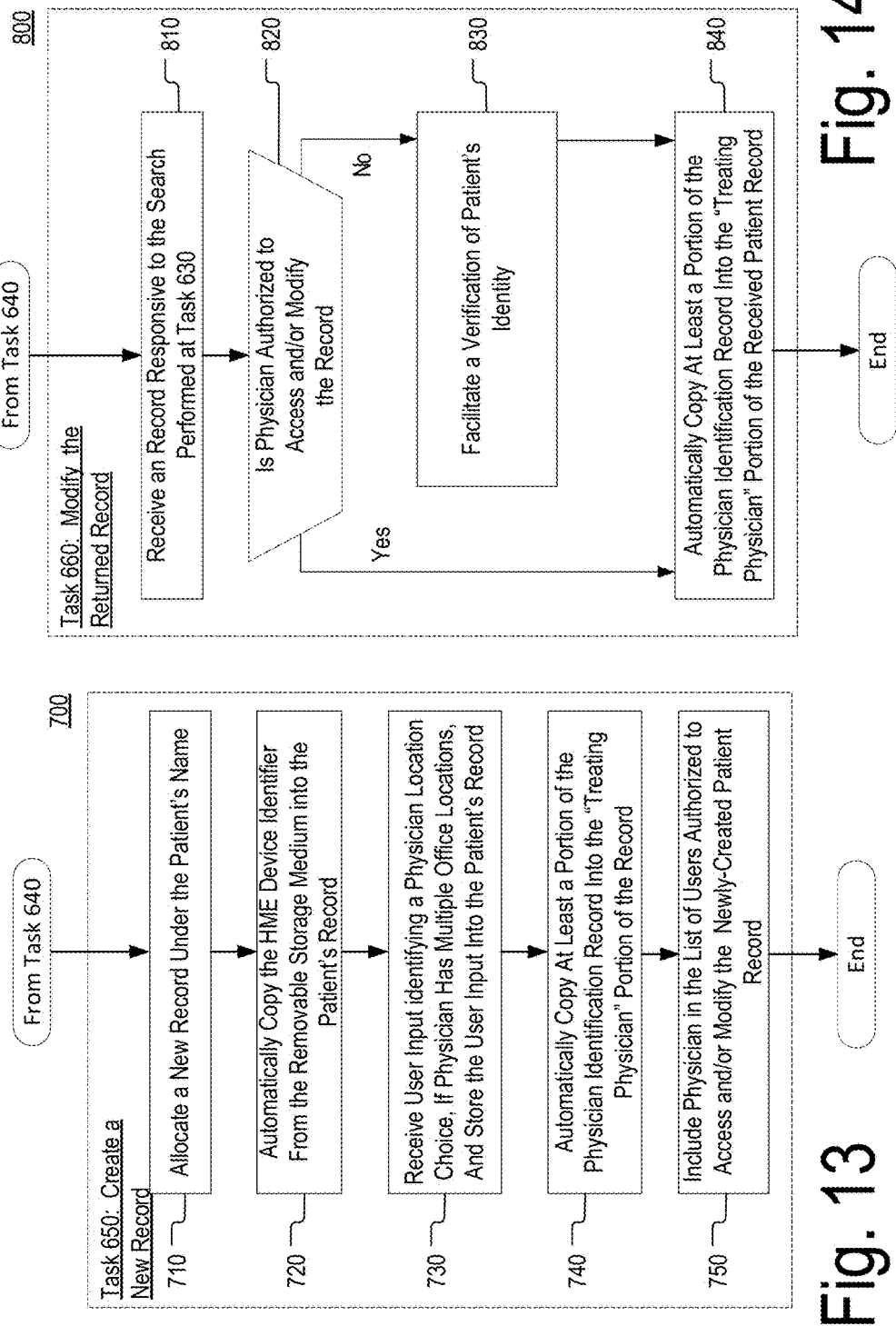

SYSTEM AND METHOD FOR MEDICAL DEVICE IDENTIFIER

1 CROSS REFERENCE TO RELATED APPLICATIONS

This application claims the benefit of the filing date of U.S. Provisional Patent Application No. 61/708,437 filed Oct. 1, 2012, the disclosure of which is hereby incorporated herein by reference.

2 BACKGROUND OF THE TECHNOLOGY 2.1 Field of the Technology

The present technology relates to device identifiers, such as a serial number, of home medical equipment (HME) devices. The technology may be implemented in conjunction with devices for the diagnosis, treatment and/or amelioration of respiratory disorders, and to procedures to prevent respiratory disorders. Thus, the present technology may relate to medical devices, and their use for treating respiratory disorders and for preventing respiratory disorders.

2.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

2.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2: 2007, 10 cm $H_2O$ pressure at 1 m)

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10 cm $H_2O$)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.4 PAP Device

The air at positive pressure is typically supplied to the airway of a patient by a PAP device such as a motor-driven blower. The outlet of the blower is connected via a flexible delivery conduit to a patient interface as described above.

2.2.5 Sleep Detection

Sleep information may be useful for treating and/or diagnosing respiratory issues or may simply be useful for monitoring health.

2.2.6 Home Medical Equipment

Home medical equipment (HME) devices is a category of medical devices used for the treatment of patients in their homes. HME devices are usually prescribed by physicians and dispensed by HME providers. Patient records regarding the use of HME devices may be maintained in centralized medical databases, such as the EASYCARE ONLINE™ database. Such centralized databases may give access to patients' records to both physicians and HME providers.

In order to manage a patient's treatment effectively, HME providers and physicians need to work with the same set of patient records. However, when a physician or HME provider is attempting to access a patient record associated with an HME device for the first time, he or she may create duplicate records. For example, the HME provider or physician may mistype information used to search for the records and as a result they may fail to find existing records that are associated with the HME device. Without realizing that a mistake has been made, the HME provider or physician may assume that a record associated with the HME device has not been created yet and, as a result, proceed to create a new patient record, thereby causing duplicate records to exist.

Previous attempts to provide controlled access to patients' records and prevent the creation of duplicates have been associated with the introduction of systems of unique identifiers that had to be manually recorded in the patient's file. Many such systems have been found to be complex and unreliable. Accordingly, the need still exists for a robust and reliable method for managing data associated with a home medical equipment (HME) device provided to a patient by providing a convenient, but at the same time well controlled, access for creating and updating patients' records stored in a centralized medical database.

BRIEF SUMMARY OF THE TECHNOLOGY

The present technology is directed towards providing health or medical devices and may optionally be used with devices for the diagnosis, amelioration, treatment, and/or prevention of respiratory disorders having one or more of improved comfort, cost, efficacy, ease of use and manufacturability.

For example, one aspect of the technology relates to a frequent situation where a patient has already visited an HME provider (also referred simply as an HME), however, when the patient later visits a physician the HME still has not created a patient record in a record management system or has created such a record, but has not associated it with the corresponding physician. According to this aspect, a method for managing data associated with a home medical equipment (HME) device provided to a patient may involve storing an HME device identifier on a removable storage medium, such as an SD card or other type of memory device. When the patient received the device from the HME, the device had already included the removable storage medium having the unique identifier stored on it. As in this case the HME had failed to create a patient record, as this should be done by the physician. During the patient's visit to the physician, the physician may receive the storage medium from the patient and connect it to the web based record management system. For that purpose, the physician will first log on to the record management system. As described further herein, various means, such as a Java® applet, may for example be configured to facilitate the interaction between such a user and the record management system. The physician log on may indicate to the record management system the identity of the Physician organization that accesses the system. The record management system may receive the identification of the device and check if such an identifier is already registered on the data management database. When no such record has been previously created by the HME provider, the physician has to create a new patient record in the record management system. During the creation of the record, the identity of the Physician organization and the HME identification (e.g., number) of the device are automatically associated with the patient record. Data of the particular physician from the respective Physician organization, who has admitted the patient, may also be received and stored on the system. As at least his organization is automatically associated with the patient's record, the physician then has full access to the record and can, for example, upload any sleep data or other health data saved on the memory device. The physician can then provide the removable storage medium to the patient.

If the patient now takes the storage medium back to the HME provider, the HME provider may use the HME device identifier stored on the medium to locate the patient record created by the physician. The HME provider is also asked to verify the identity of the patient. For this purpose, the HME provider has to verify that the patient's name and date of birth, as recorded in the record management system, are identical to those of the patient who provided the storage medium. Once the patient identity is verified, the HME is also automatically associated with the patient's record, by the details of the HME organization, location and, possibly, the identity of the HME, being received by the system. Once associated with the record, the HME provider can view and modify the record. Afterwards, the HME provider may dispense the HME device back to the patient.

In another aspect, a method is provided for use in situations where a patient visits a physician after obtaining an HME device from an HME provider. According to this aspect, when dispensing the HME device, the HME provider may create a patient record that associates the patient with an HME device identifier stored on a removable storage medium. During the creation of the record, the HME is automatically associated with the record, which provides the HME with full access to the record. The HME provider may then hand over the removable storage medium to the patient along with the HME device. The patient may take the HME device to a physician and provide the removable storage medium to the physician. The physician may use the HME device identifier stored on the medium to locate the patient record created by the HME provider. Once the record is identified on the system, the physician has to verify the identity of the patient, by comparing patient's data (usually the client's name and date of birth) displayed on the screen by the system, with information obtained from the patient. Alternatively, the system may ask the physician to type the patient's details, which are then compared with these on the system. Once the identity of the patient has been positively verified, the physician is automatically associated with the system, by details of the physician's organization, organization branch/location and, possibly, the identity of the HME, being received by the system. Depending on predefined arrangements with the Physician's organization, the physician can now either only access, or access and modify the patient's data. For example, the physician can upload new data from the memory device or may modify the patient record to include information identifying the physician as the one in charge of the patient's treatment with the HME device.

In yet another aspect, when the patent record is initially set up, the unique HME device identification number may be entered either manually or be automatically extracted (e.g., by way of a barcode scanner scanning the device identification number encoded on the device, or by using wireless connectivity such as Bluetooth to connect to the device which will have the number saved in its internal memory). The HME device identifier is then transferred from the internal memory onto the removable storage medium. From this point on, either one of the physician and HME provider can perform a records search and can access the patient record based on reading the removable storage medium by using either a memory card reader (or by using a barcode scanner, if the unique identification number has been encoded on the outside of the storage medium). In either case, the HME device identifier is loaded automatically and submitted to the database that is searched. By removing the need to enter the HME device identifier manually, typographical errors are prevented from being introduced into the records search.

In yet another aspect, when either one of the physician and HME provider is given a removable storage medium containing an HME device identifier, and fails to find an existing patient record associated with the identifier, they may create a new record and associate the newly-created record with the HME device identifier. Because the HME device identifier is copied automatically, either from the removable storage medium or wirelessly, when records searches are performed, the possibility of false negative searches due to a mistyped HME device identifier is reduced. This in turn increases the likelihood that a patient record associated with the HME device identifier is going to be found if such exists, thereby decreasing the likelihood of duplicate records being created.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

3.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

3.2 Therapy 3.2.1 Respiratory System

Figure 2A:
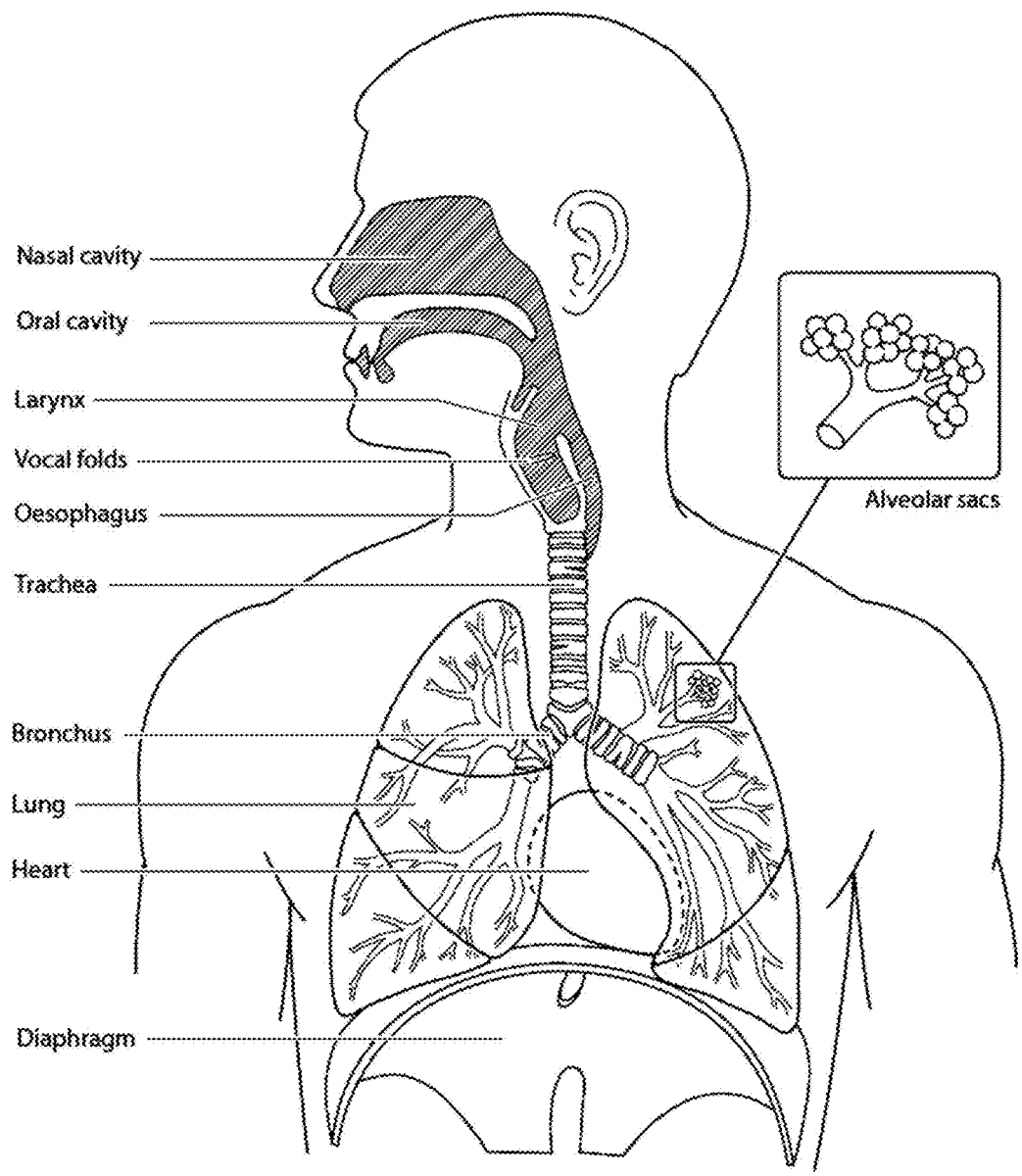

FIG. 2a shows an overview of a human respiratory system including the nasal and oral cavities, the larynx, vocal folds, oesophagus, trachea, bronchus, lung, alveolar sacs, heart and diaphragm.

Figure 2B:
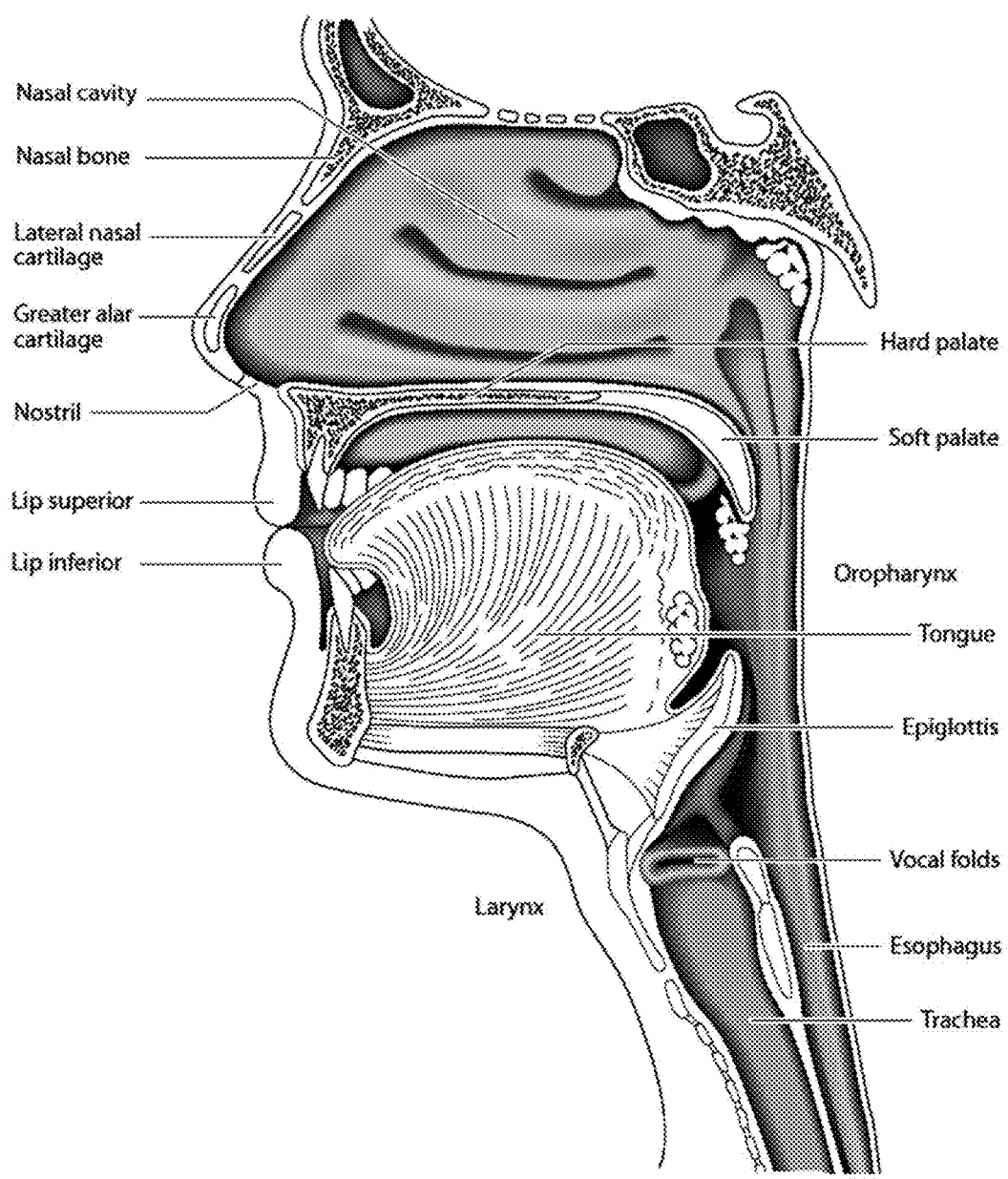

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

3.3 Patient Interface

Figure 3:
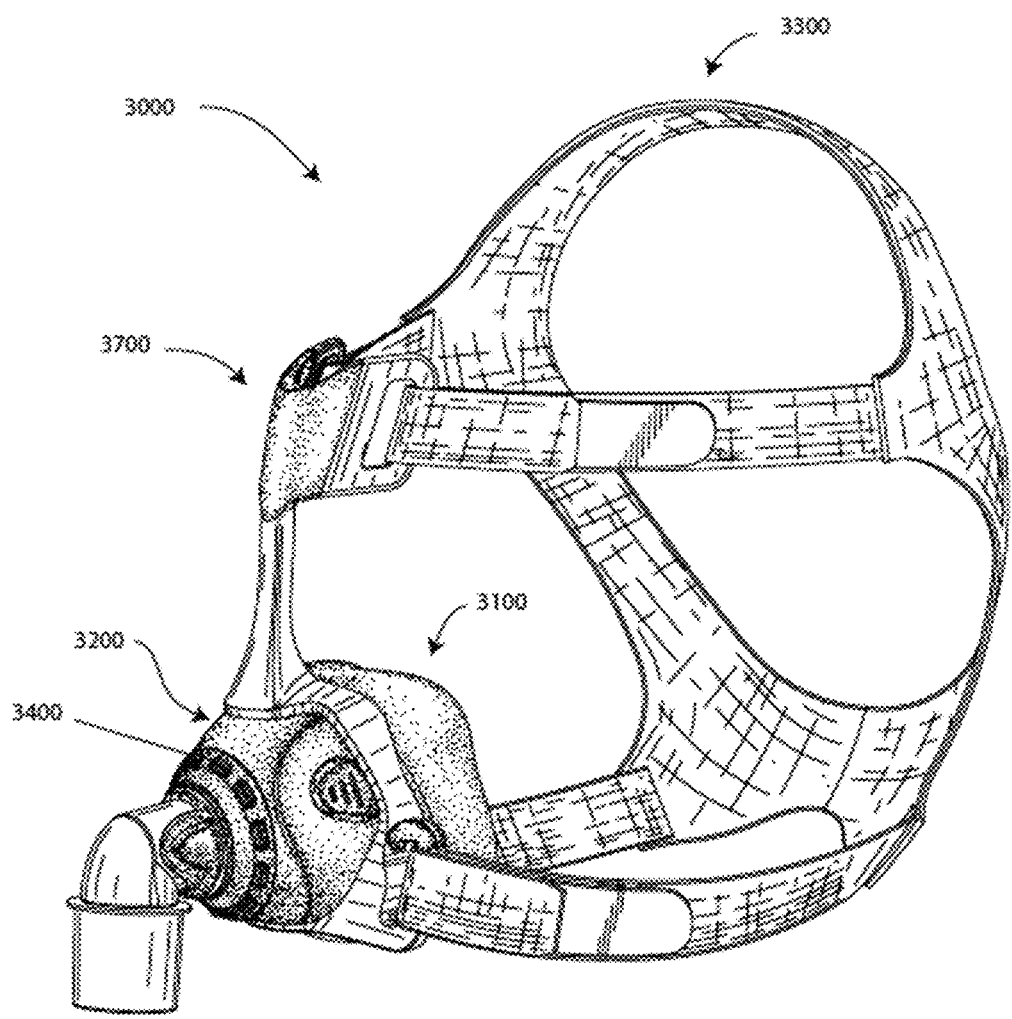

FIG. 3 shows a patient interface in accordance with one form of the present technology.

3.4 PAP Device

Figure 4A:
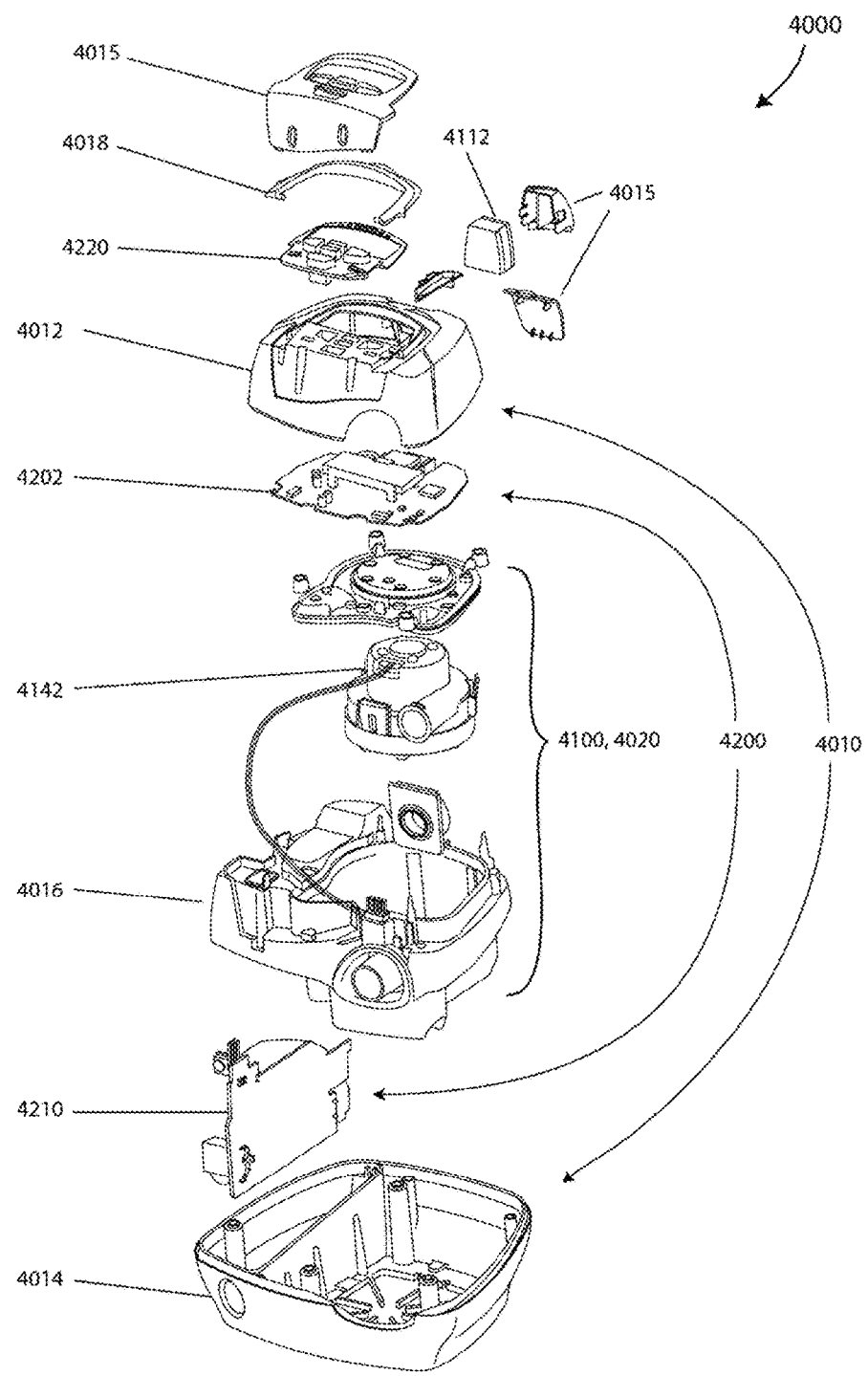

FIG. 4a shows a PAP device in accordance with one form of the present technology.

Figure 4B:
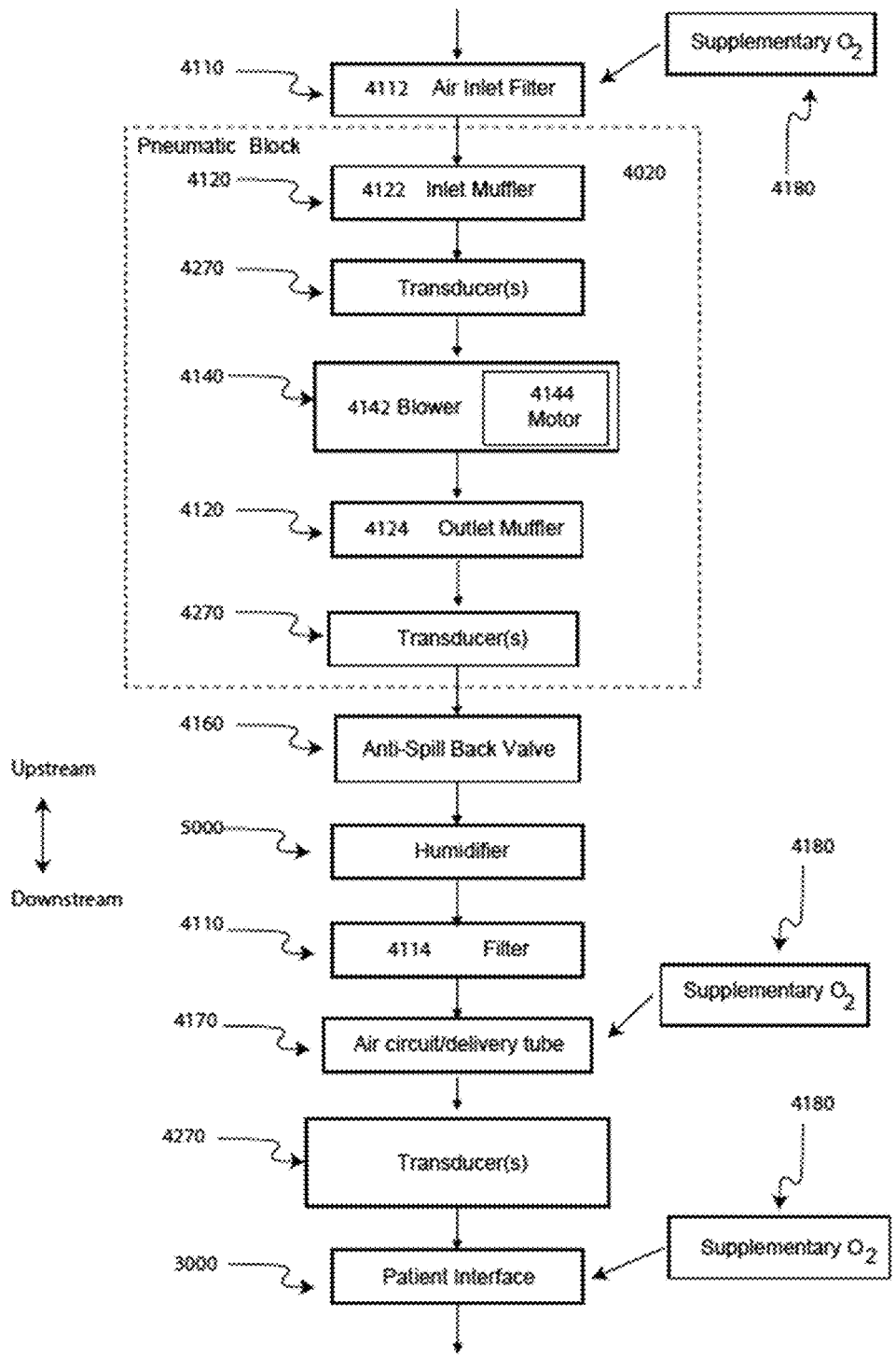

FIG. 4b shows a schematic diagram of the pneumatic circuit of a PAP device in accordance with one form of the present technology. The directions of upstream and downstream are indicated.

Figure 4C:
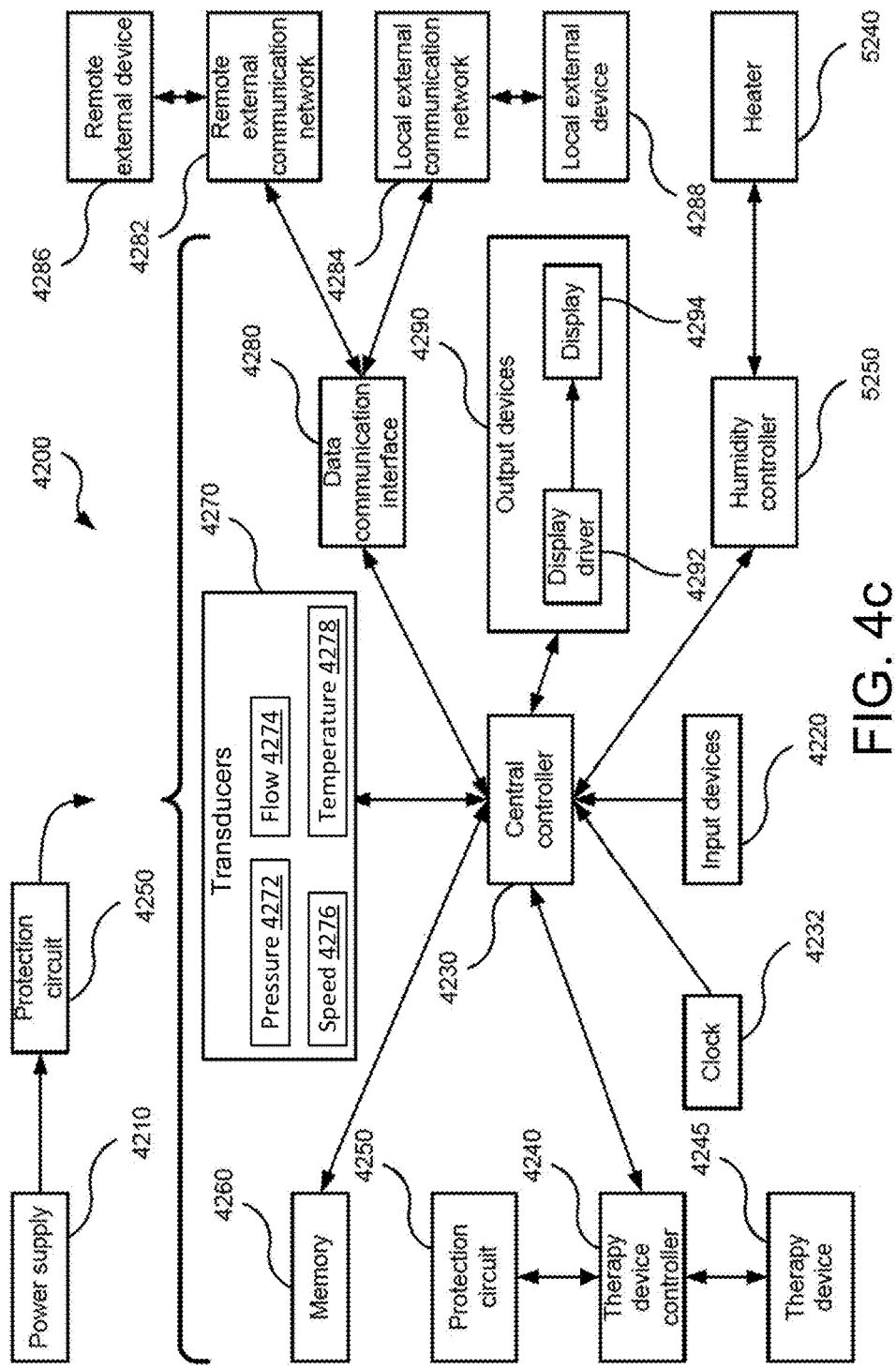

FIG. 4c shows a schematic diagram of the electrical components of a PAP device in accordance with, one aspect of the present technology.

Figure 4D:
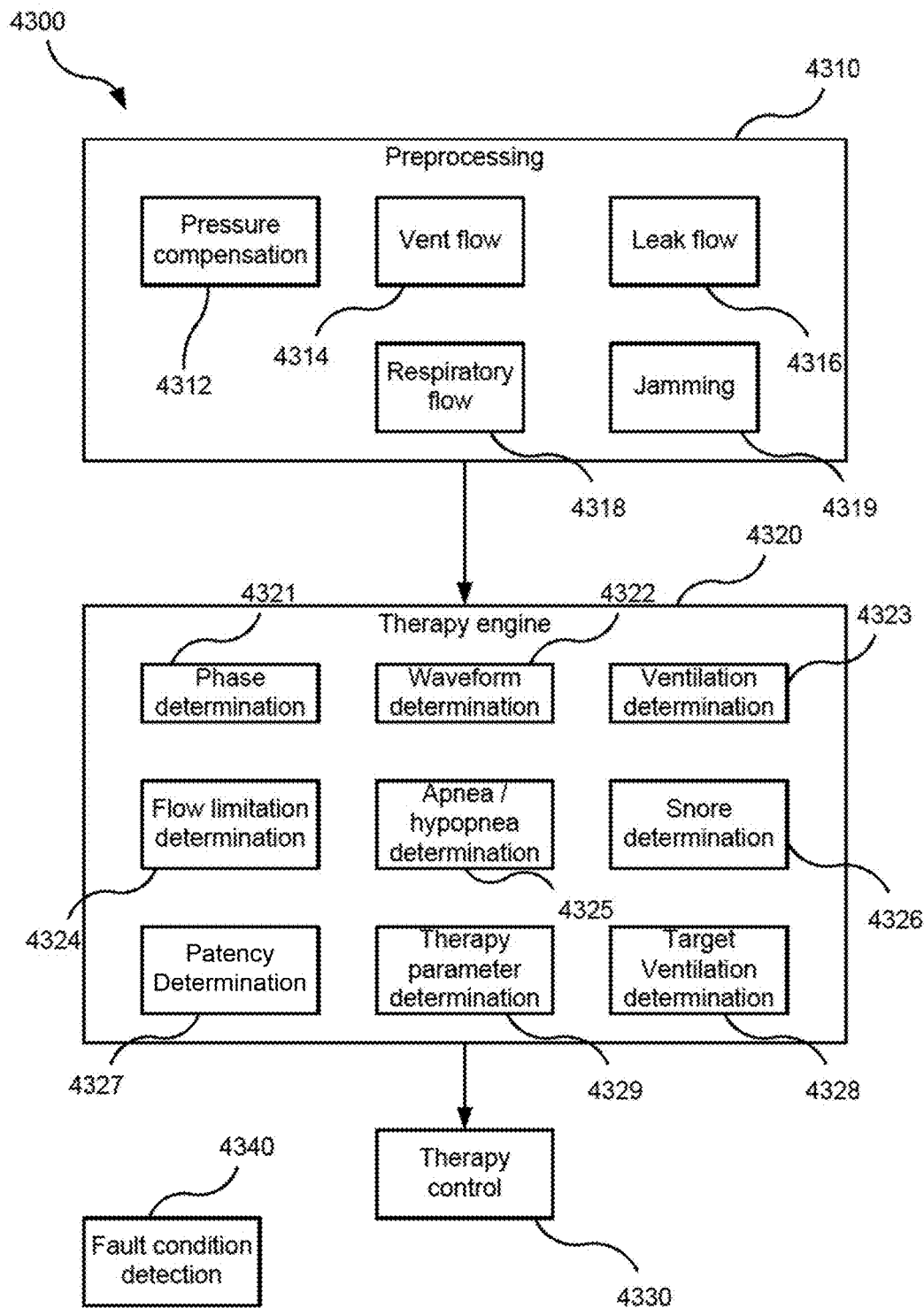

FIG. 4d shows a schematic diagram of example processes or algorithms implemented in a PAP device in accordance with an aspect of the present technology. In this figure, arrows with solid lines indicate an actual flow of information, for example via an electronic signal.

3.5 Humidifier

Figure 5:
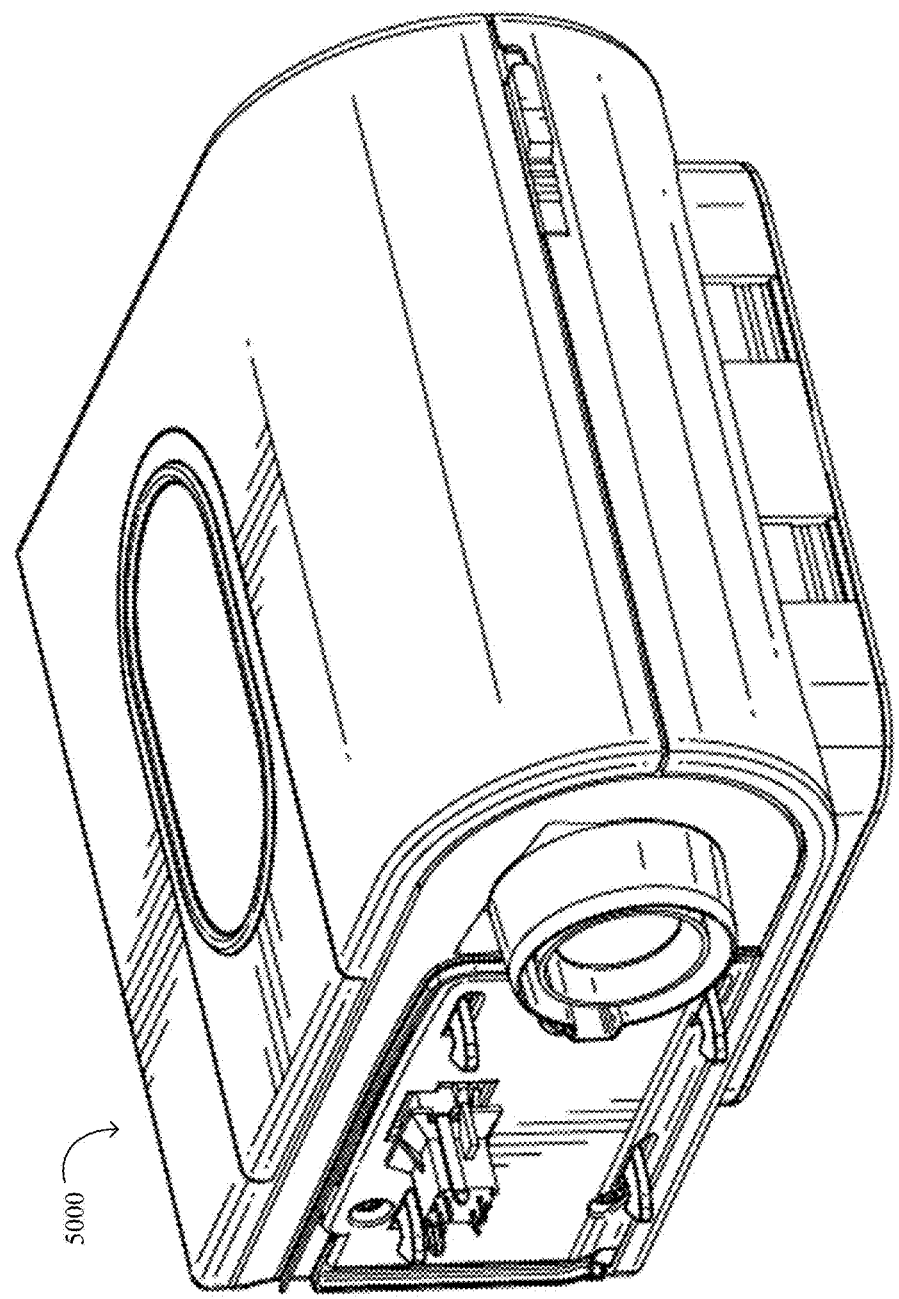

FIG. 5 shows an example humidifier in accordance with one aspect of the present technology.

3.6 Breathing Waveforms

Figure 6A:
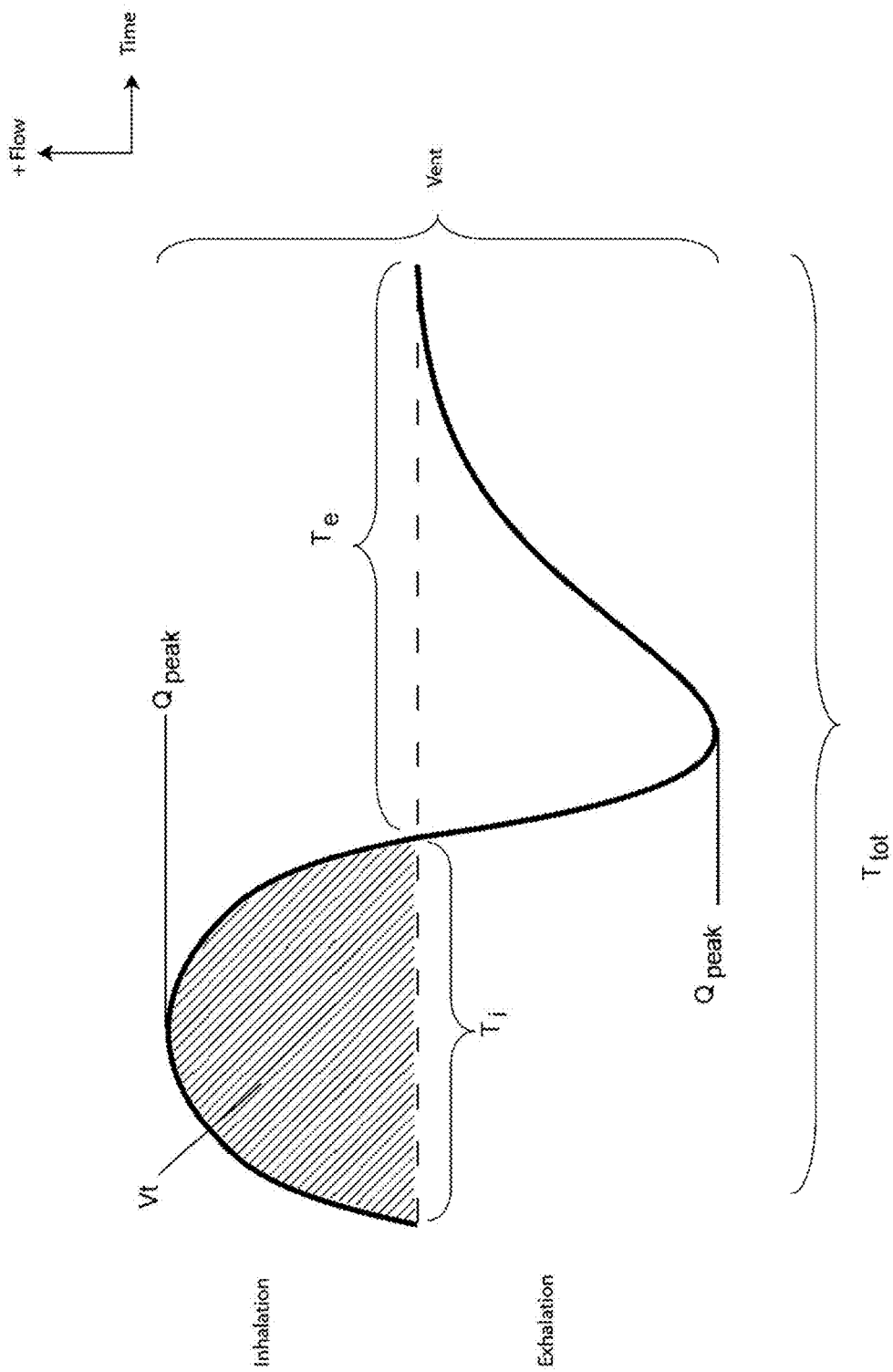

FIG. 6a shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

Figure 6B:
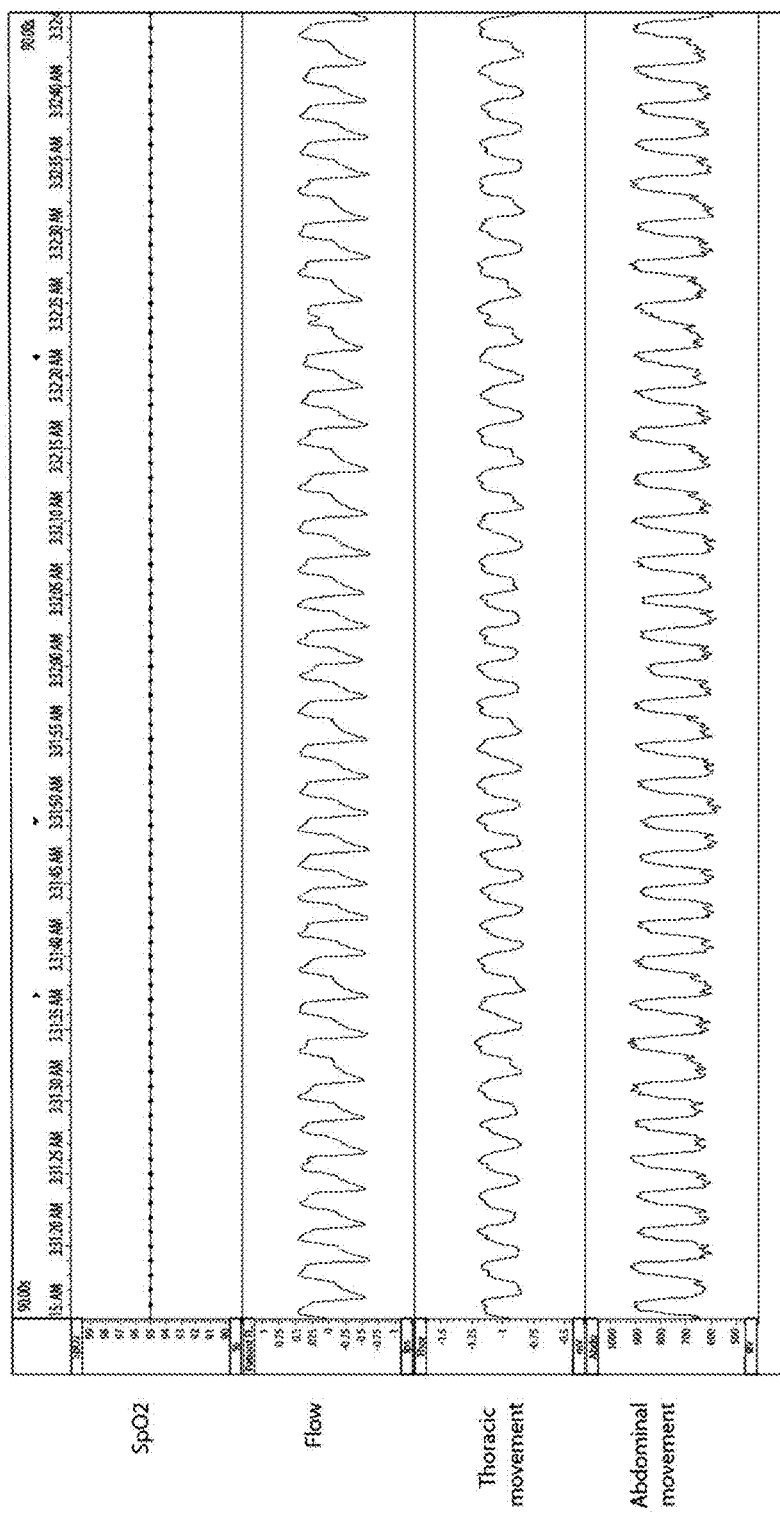

FIG. 6b shows a patient during Non-REM sleep breathing normally over a period of about ninety seconds, with about 34 breaths, being treated with Automatic PAP, and the mask pressure being about 11 cmH$_2$O. The top channel shows oximetry (SpO2), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

Figure 6C:
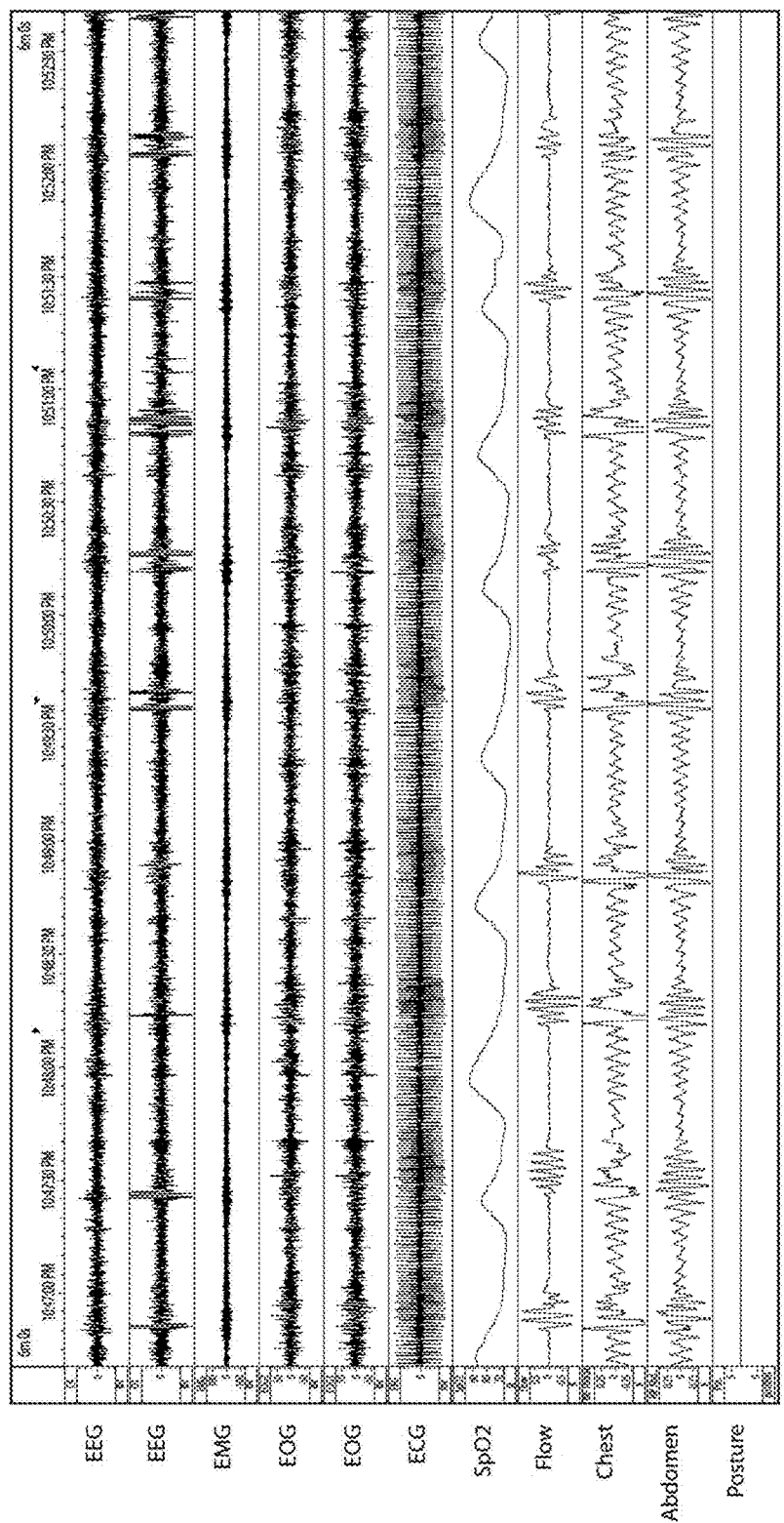

FIG. 6c shows polysomnography of a patient before a treatment. There are eleven signal channels from top to bottom with a 6 minute horizontal span. The top two channels both are EEG (electoencephalogram) from different scalp locations. Periodic spikes in second represent cortical arousal and related activity. The third channel down is submental EMG (electromyogram). Increasing activity around time of arousals represent genioglossus recruitment. The fourth & fifth channels are EOG (electro-oculogram). The sixth channel is an electocardiogram. The seventh channel shows pulse oximetry (SpO2) with repetitive desaturations to below 70% from about 90%. The eighth channel is respiratory airflow using nasal cannula connected to differential pressure transducer. Repetitive apneas of 25 to 35 seconds alternating with 10 to 15 second bursts of recovery breathing coinciding with EEG arousal and increased EMG activity. The ninth shows movement of chest and tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

Figure 6D:
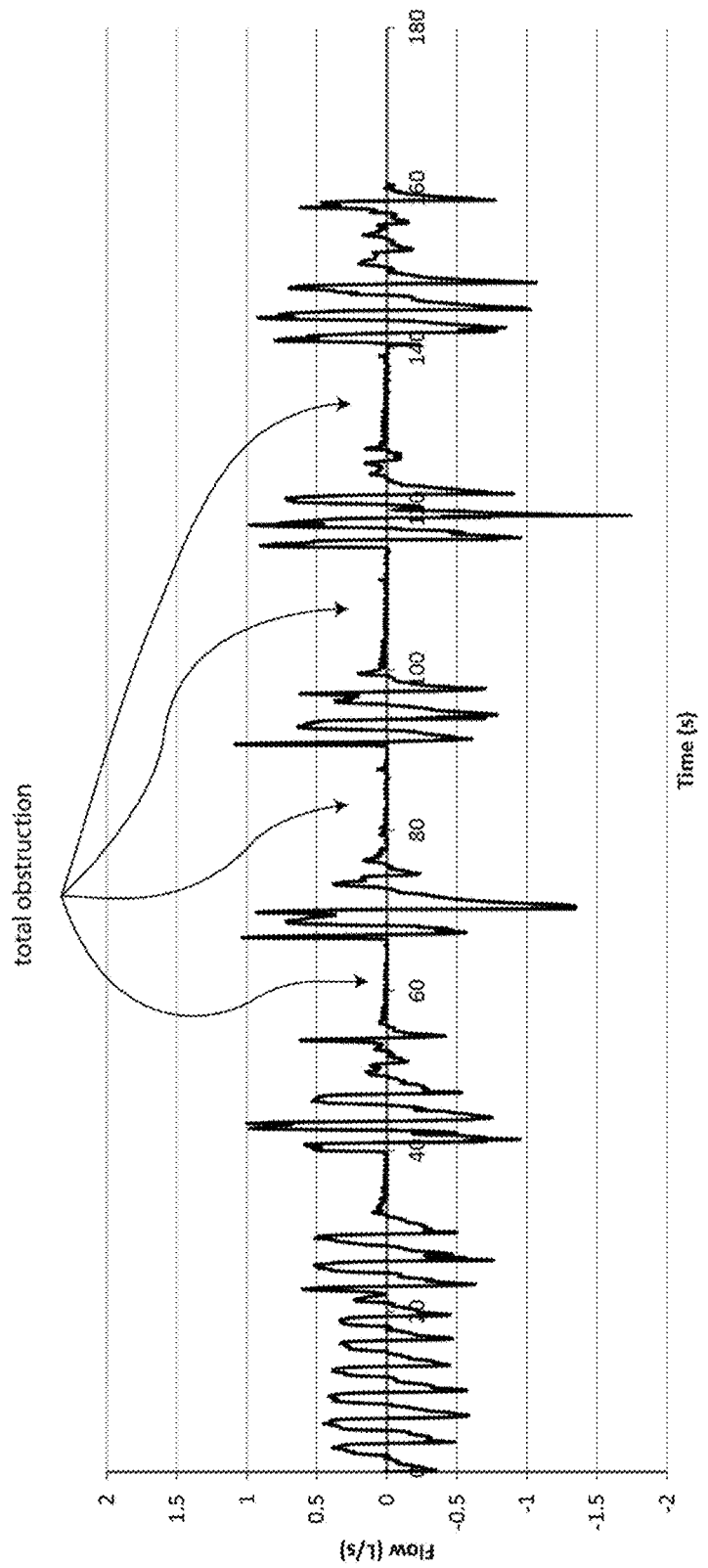

FIG. 6d shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

Figure 6E:
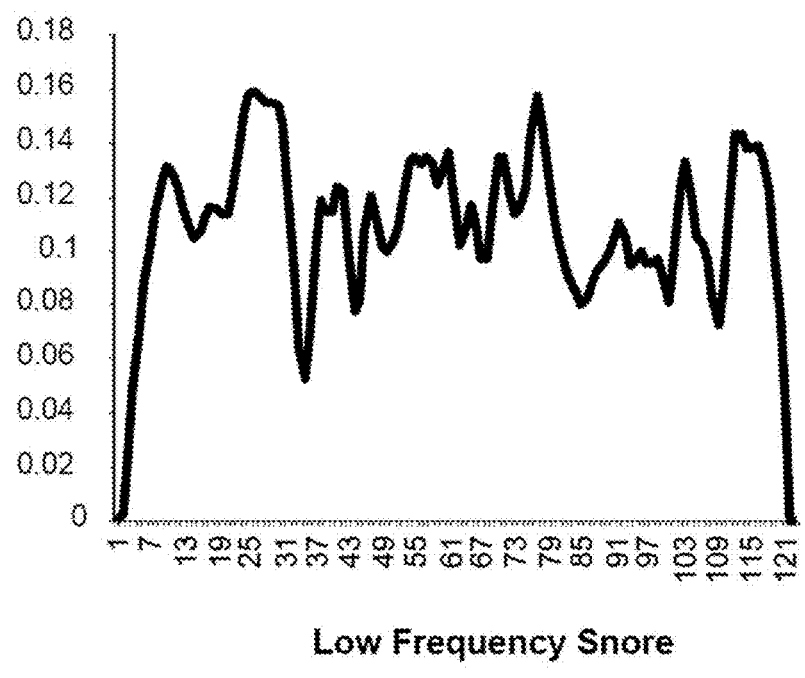

FIG. 6e shows a scaled inspiratory portion of a breath where the patient is experiencing low frequency inspiratory snore.

Figure 6F:
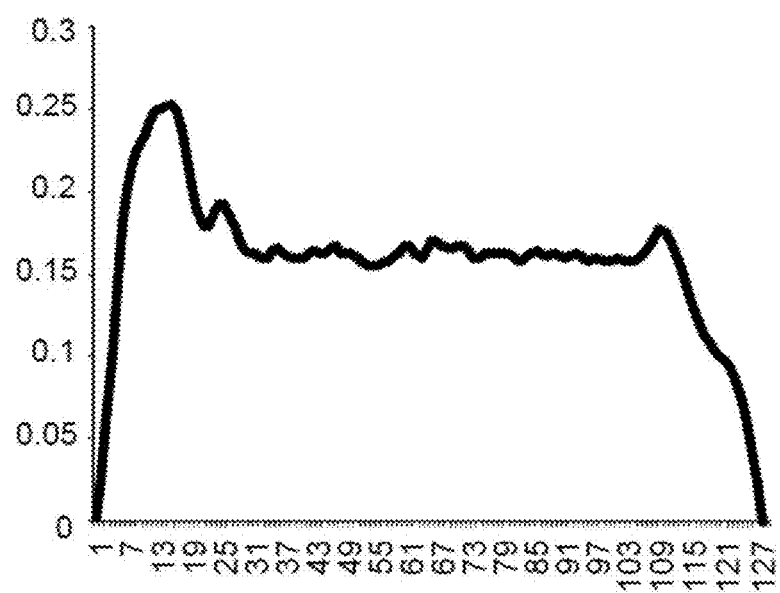

FIG. 6f shows a scaled inspiratory portion of a breath where the patient is experiencing an example of flattened inspiratory flow limitation.

Figure 6G:
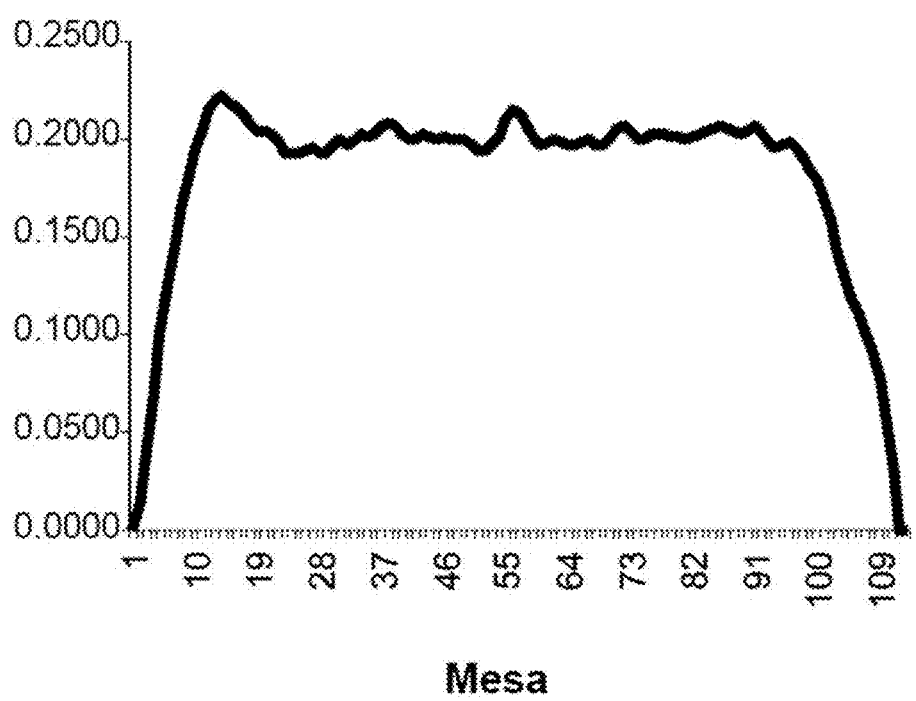

FIG. 6g shows a scaled inspiratory portion of a breath where the patient is experiencing an example of "mesa" flattened inspiratory flow limitation.

Figure 6H:
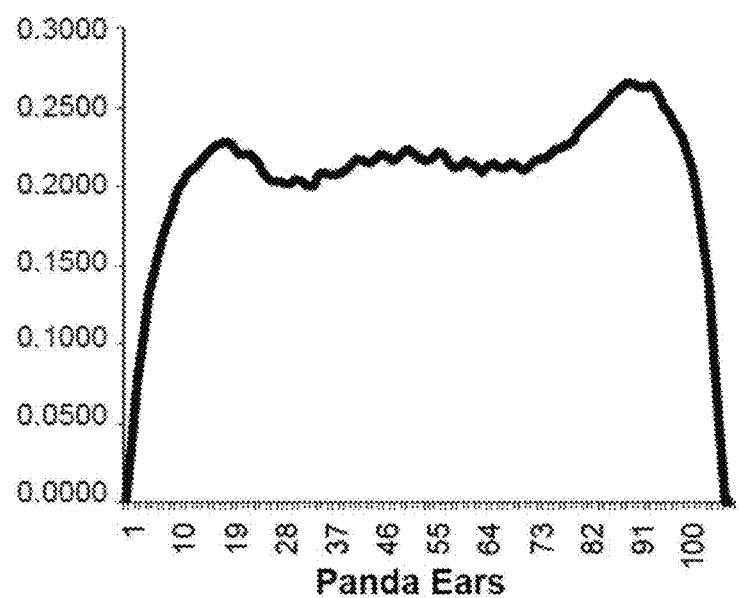

FIG. 6h shows a scaled inspiratory portion of a breath where the patient is experiencing an example of "panda ears" inspiratory flow limitation.

Figure 6I:
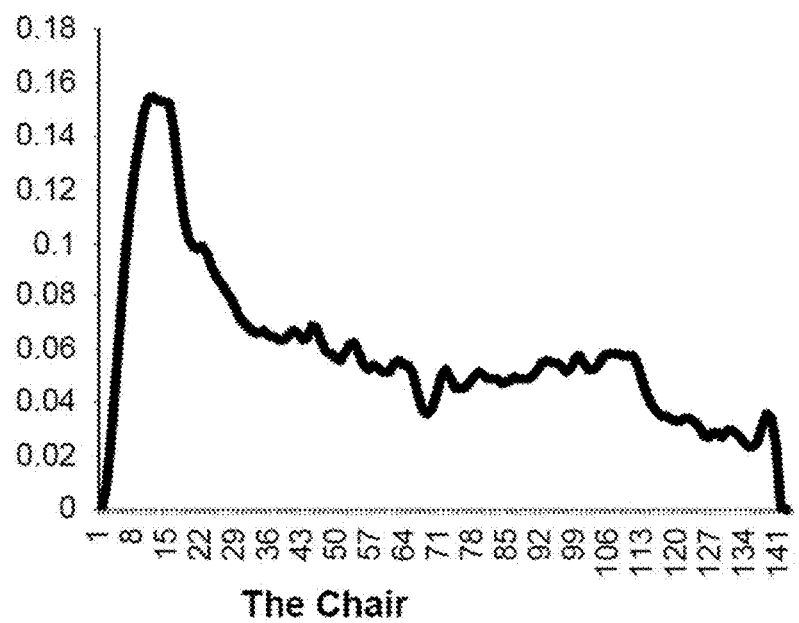

FIG. 6i shows a scaled inspiratory portion of a breath where the patient is experiencing an example of "chair" inspiratory flow limitation.

Figure 6J:
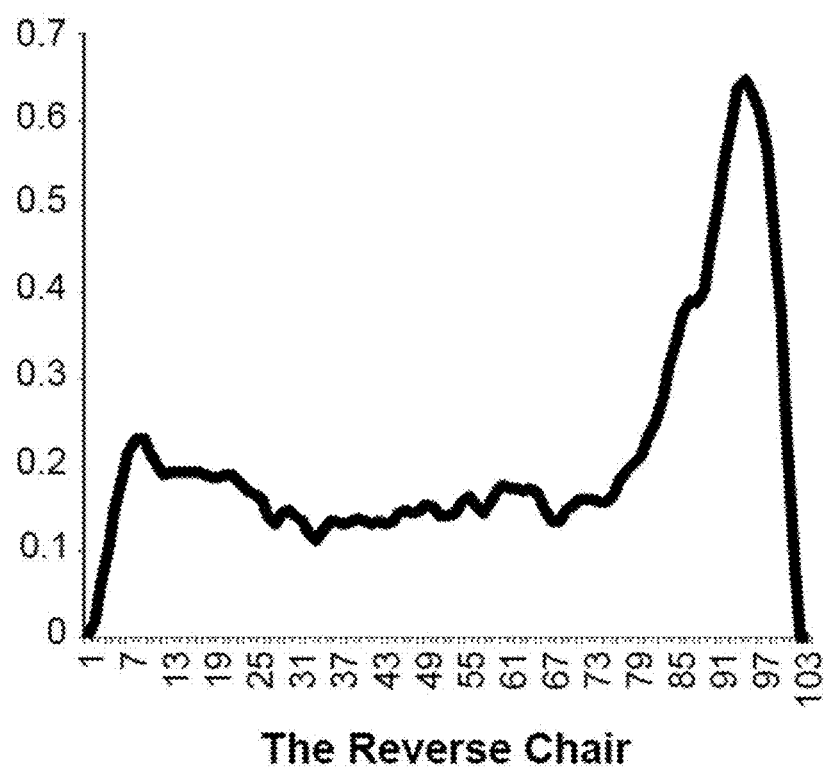

FIG. 6j shows a scaled inspiratory portion of a breath where the patient is experiencing an example of "reverse chair" inspiratory flow limitation.

Figure 6K:
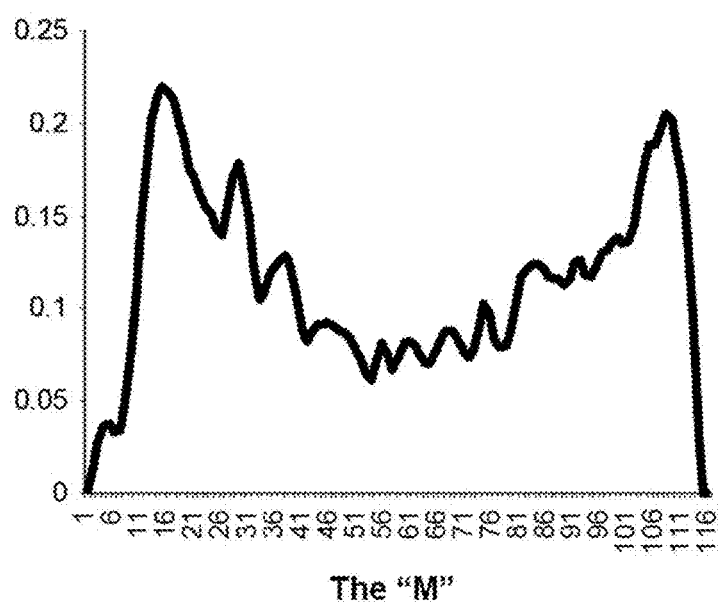
Figure 6I:
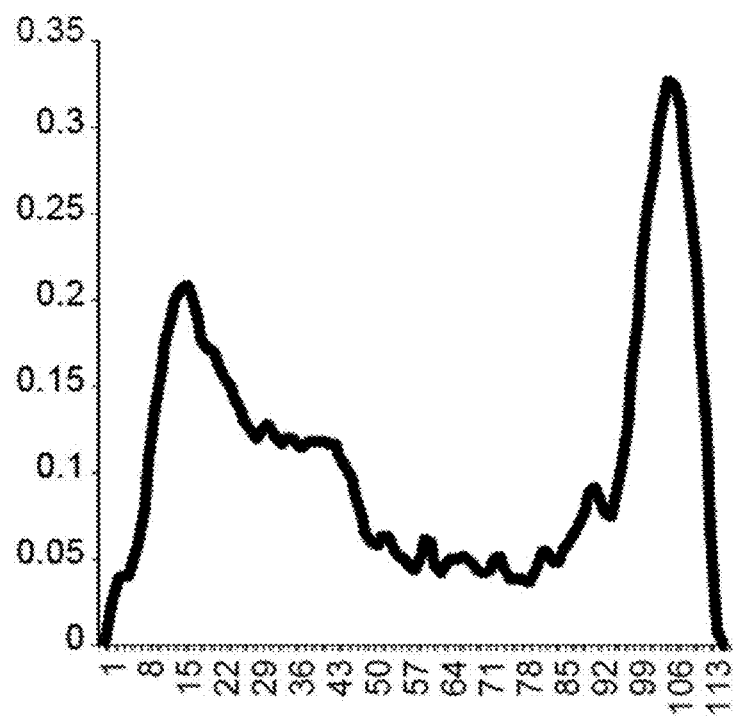

FIG. 6k shows a scaled inspiratory portion of a breath where the patient is experiencing an example of "M-shaped" inspiratory flow limitation.

FIG. 6l shows a scaled inspiratory portion of a breath where the patient is experiencing an example of severely "M-shaped" inspiratory flow limitation.

Figure 6M:
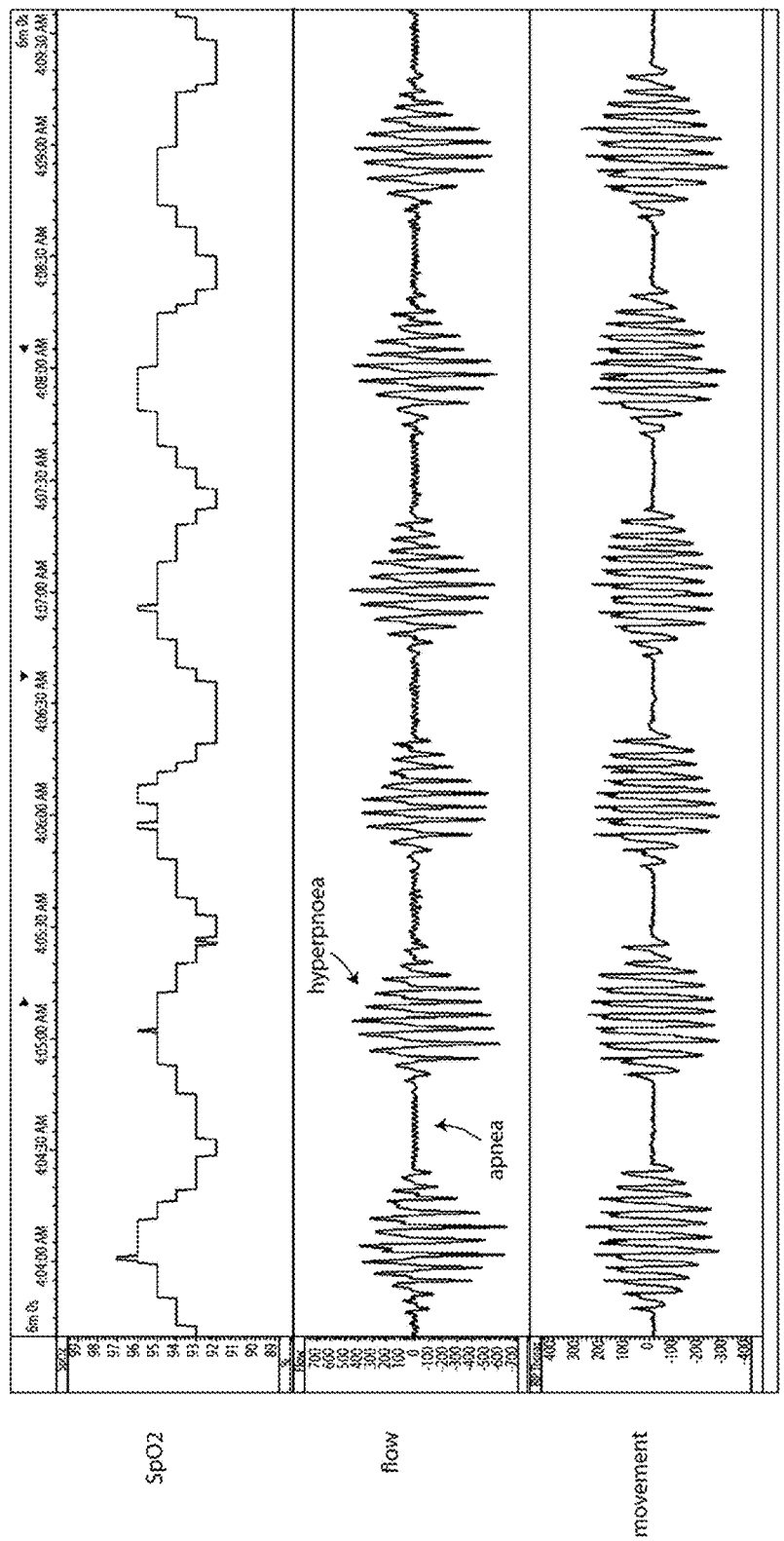

FIG. 6m shows data for a patient with Cheyne-Stokes respiration. There are three channels-oxygen saturation (SpO2), a signal indicative of flow and the third, movement. The data span six minutes. The signal representative of flow was measured using a pressure sensor connected to nasal cannulae. The patient exhibits apneas of about 22 seconds and hyperpneas of about 38 seconds. Higher frequency low amplitude oscillation during apnea is cardiogenic.

Figure 6N:
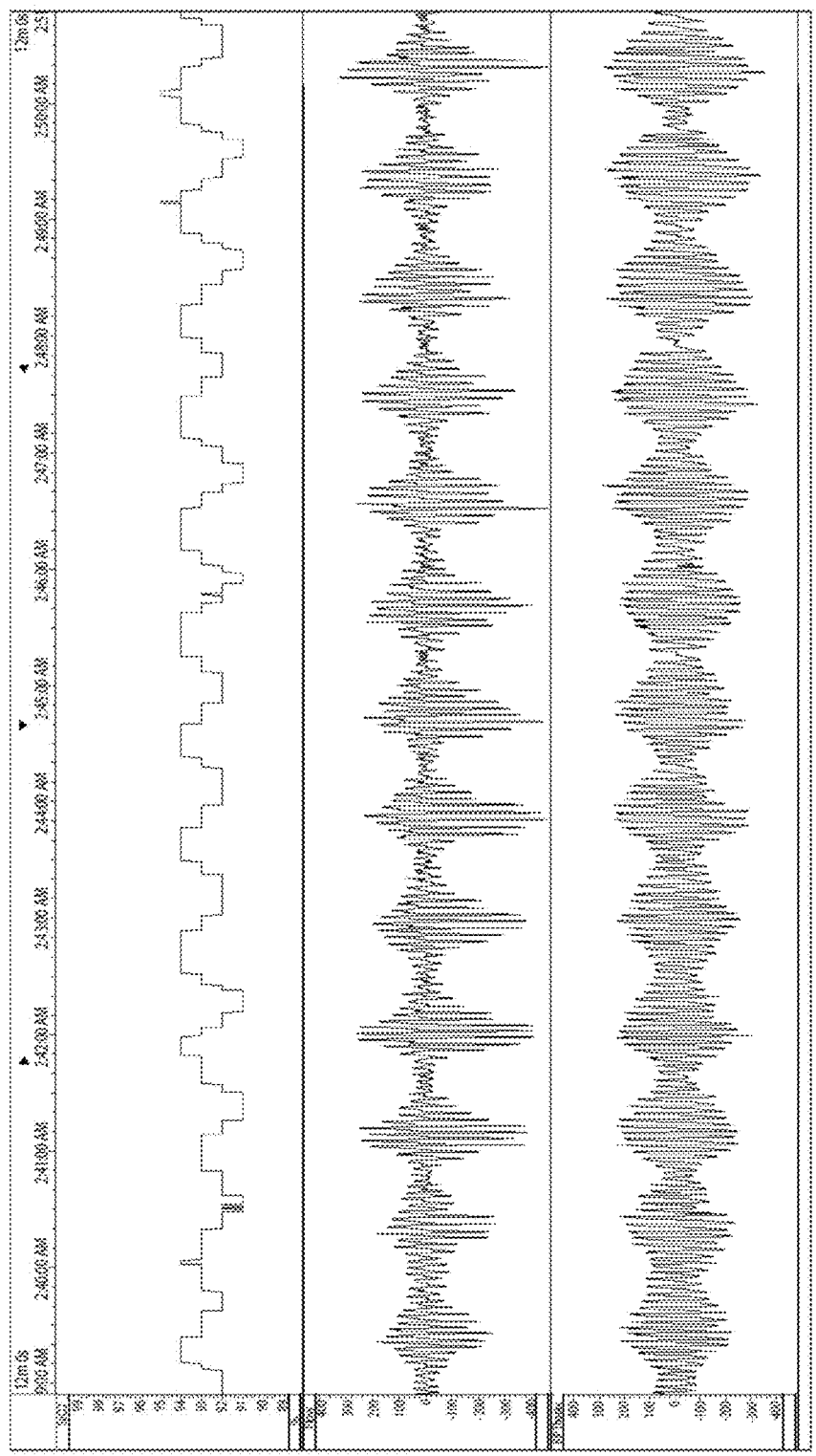

FIG. 6n shows data for a patient with another example of Cheyne-Stokes respiration, using the same three channels as in FIG. 6m. The data span ten minutes. Generally, in the flow data signal of FIG. 6n the patient is experiencing hypopneas in place of the apneas illustrated in FIG. 6m.

3.7 Serial Number Identification

Figure 7:
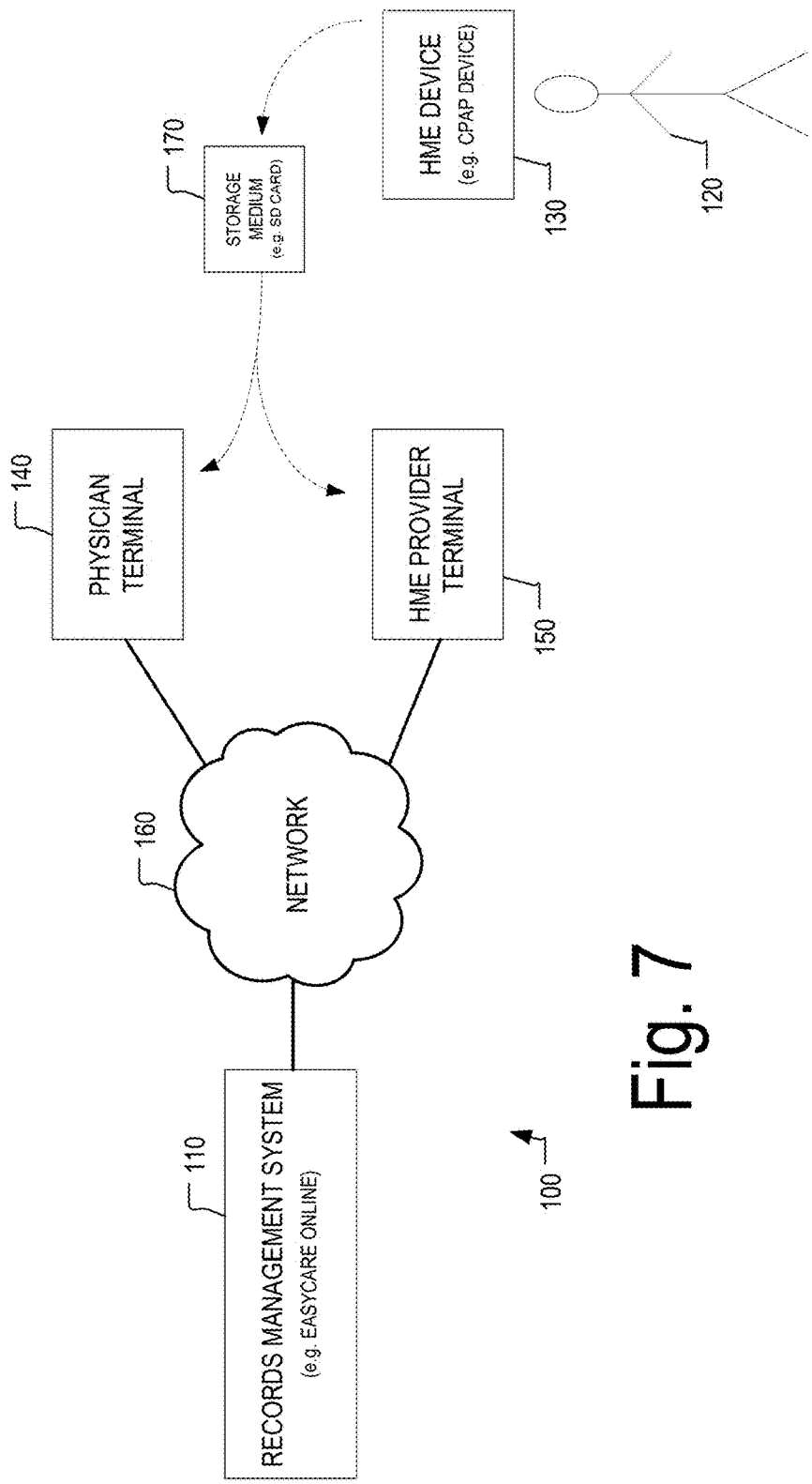

FIG. 7 depicts a schematic diagram of a patient record management system in accordance with one aspect of the disclosure.

Figure 1A:
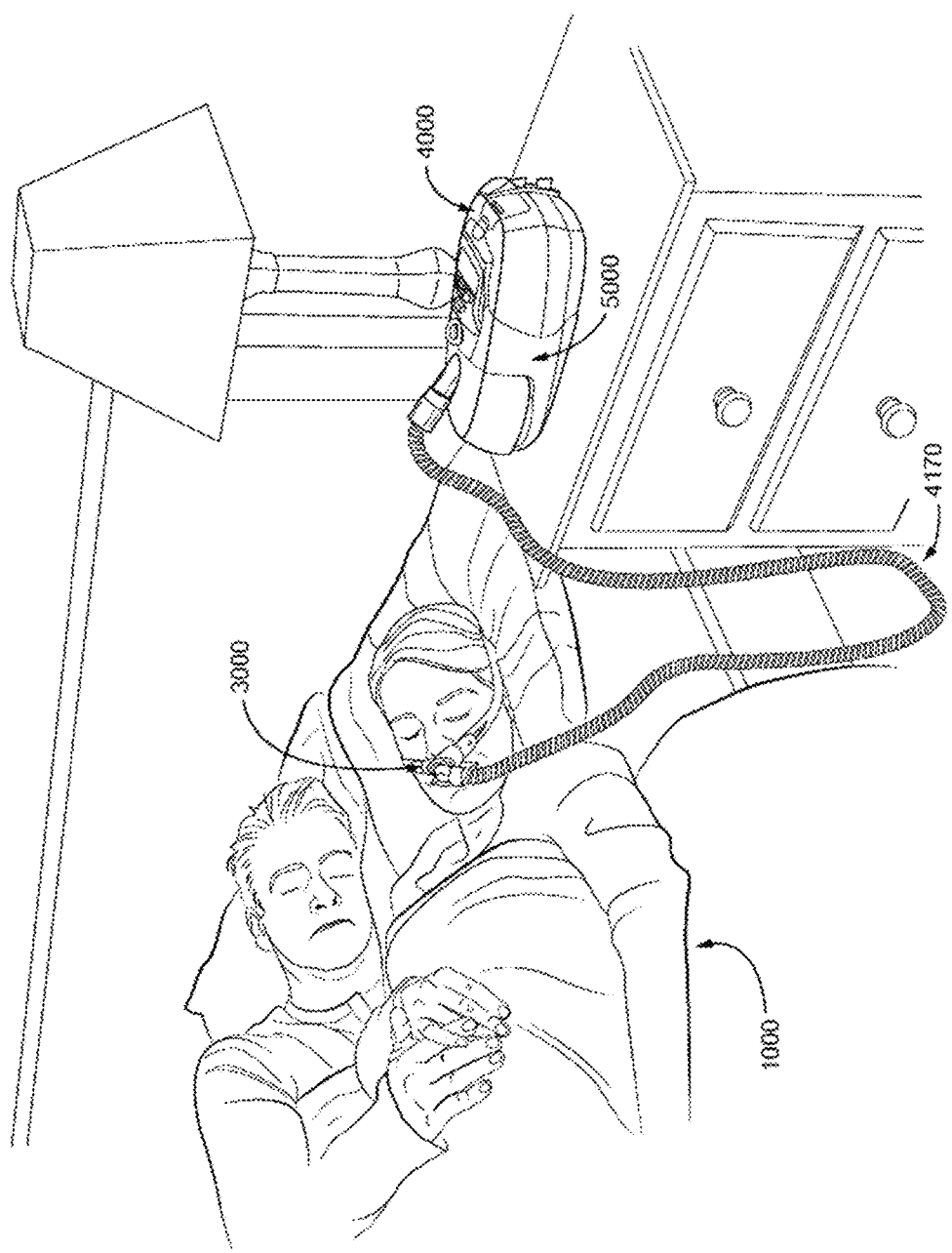
FIG. 1b shows a PAP device in use on a patient with a nasal mask.
FIG. 1c shows a PAP device in use on a patient with a full-face mask.
Figure 1B:
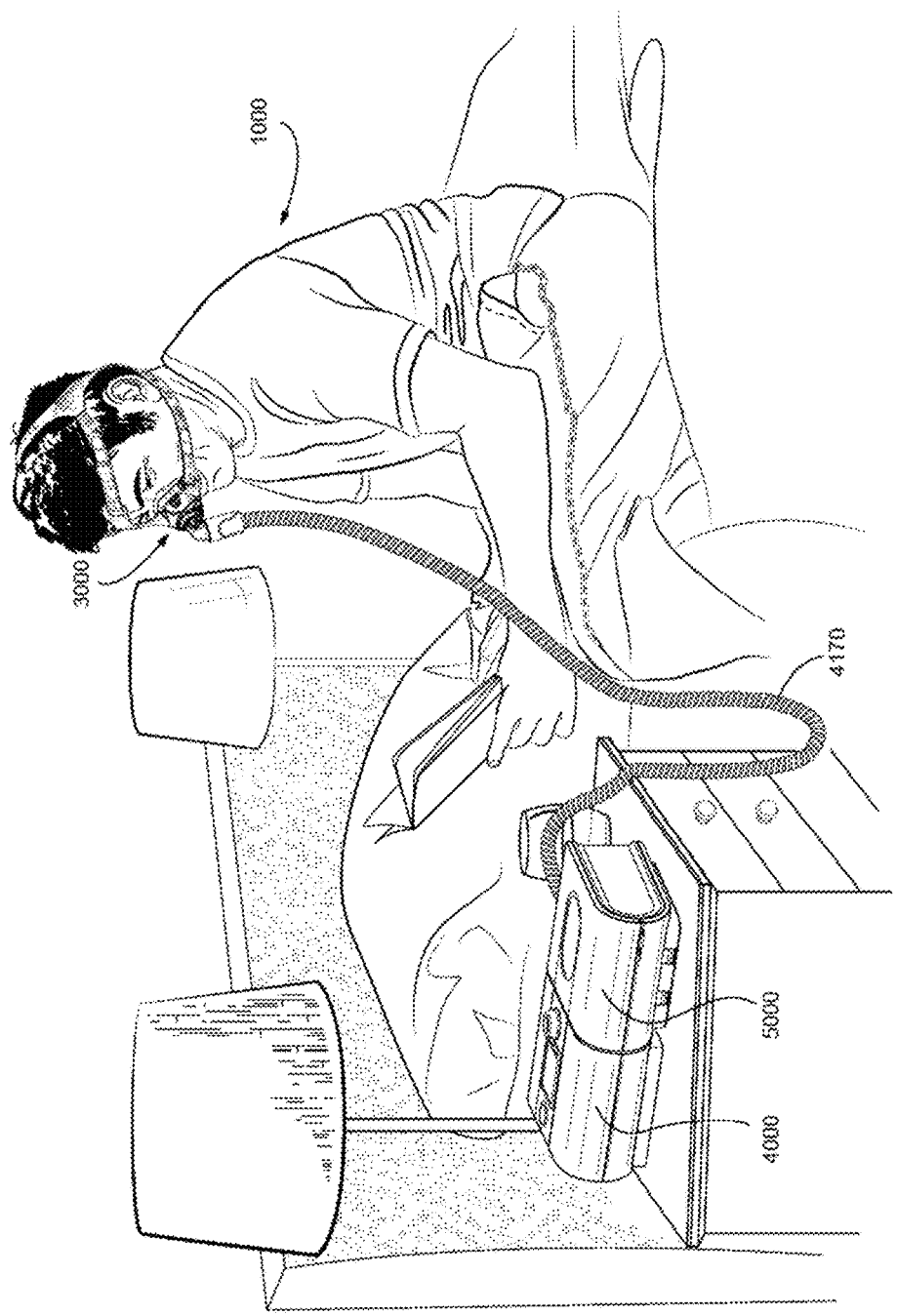
Figure 1C:
Figure 8:
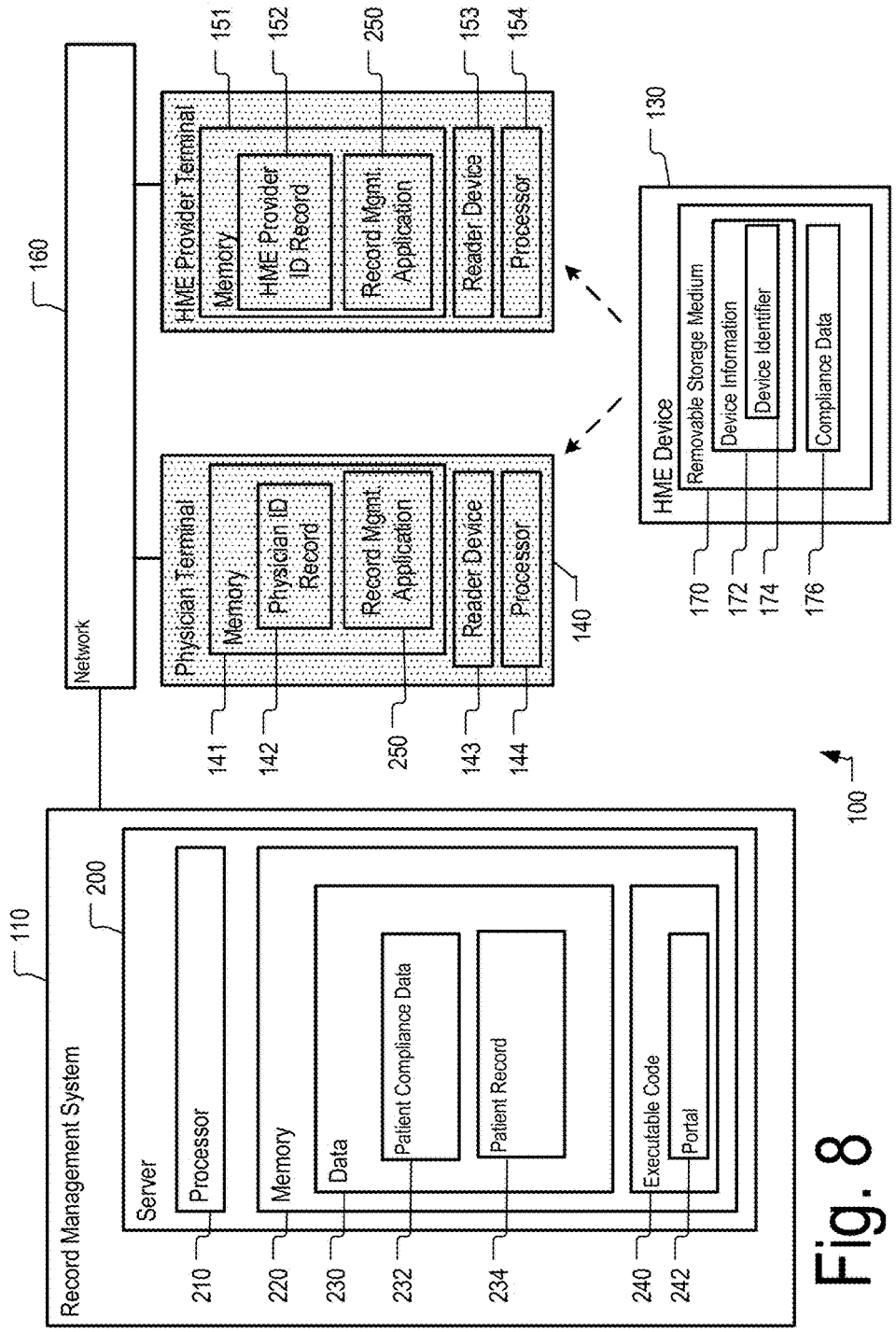

FIG. 8 depicts a schematic diagram of hardware devices used in the patient record management system of FIG. 1 in accordance with another aspect of the disclosure.

Figure 9:
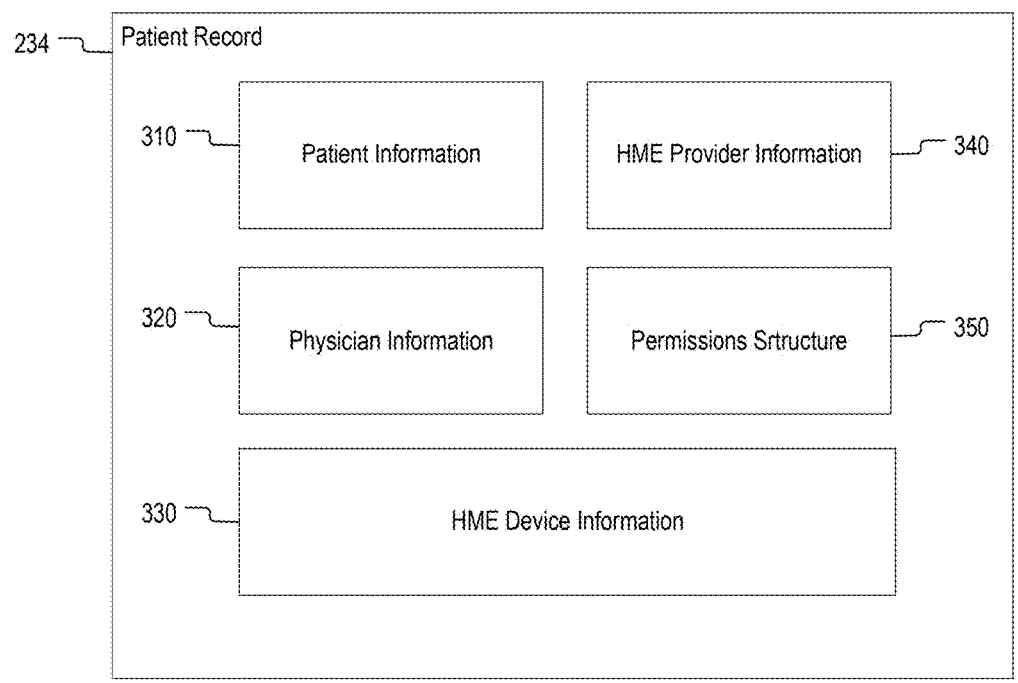

FIG. 9 depicts a schematic diagram of an electronic patient record in accordance with aspects of the disclosure.

Figure 10:
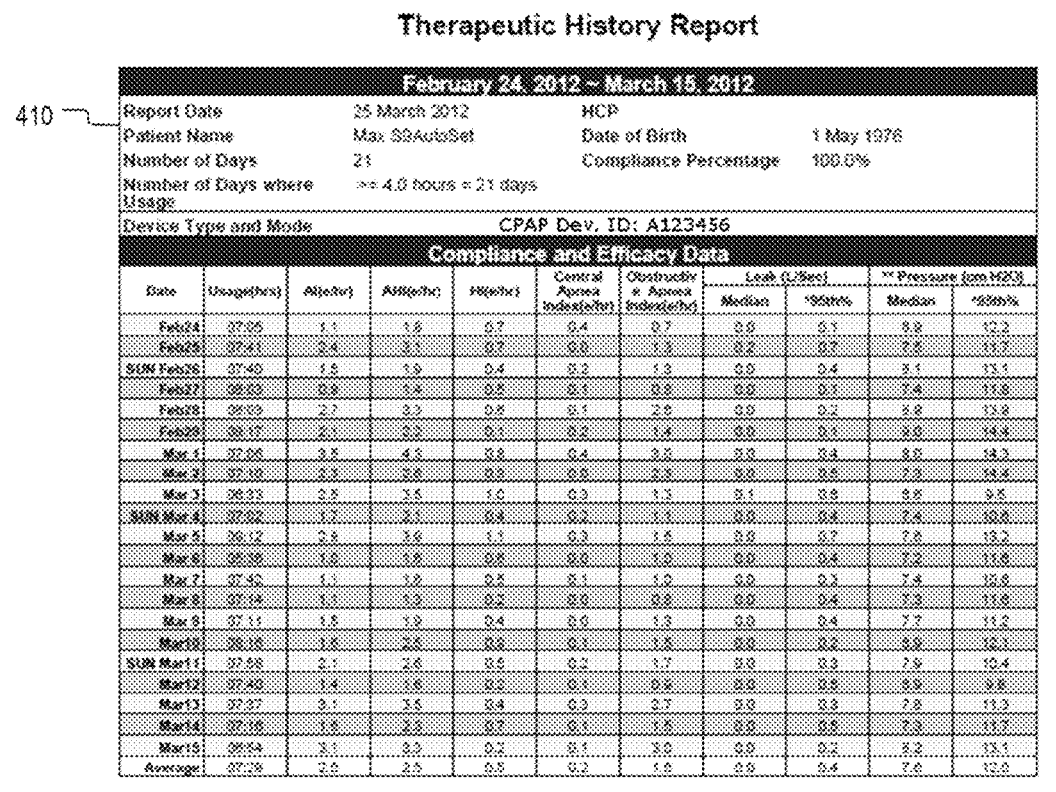

FIG. 10 depicts a schematic diagram of a sample patient compliance report in accordance with aspects of the disclosure.

Figure 11:
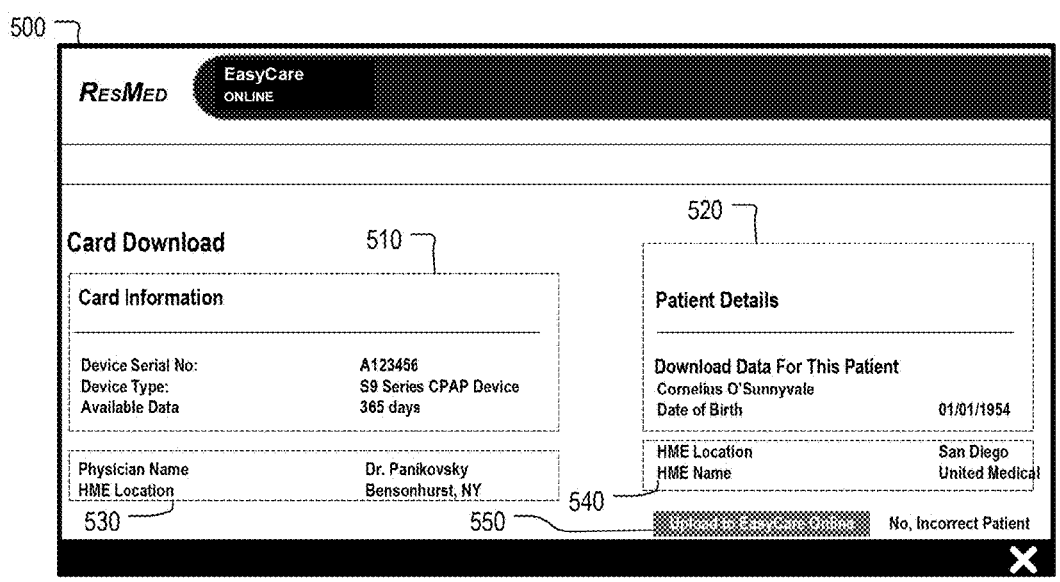

FIG. 11 depicts a schematic diagram of a user interface for modifying patient records, i.e. by adding therapy data to the patient record.

Figure 12:
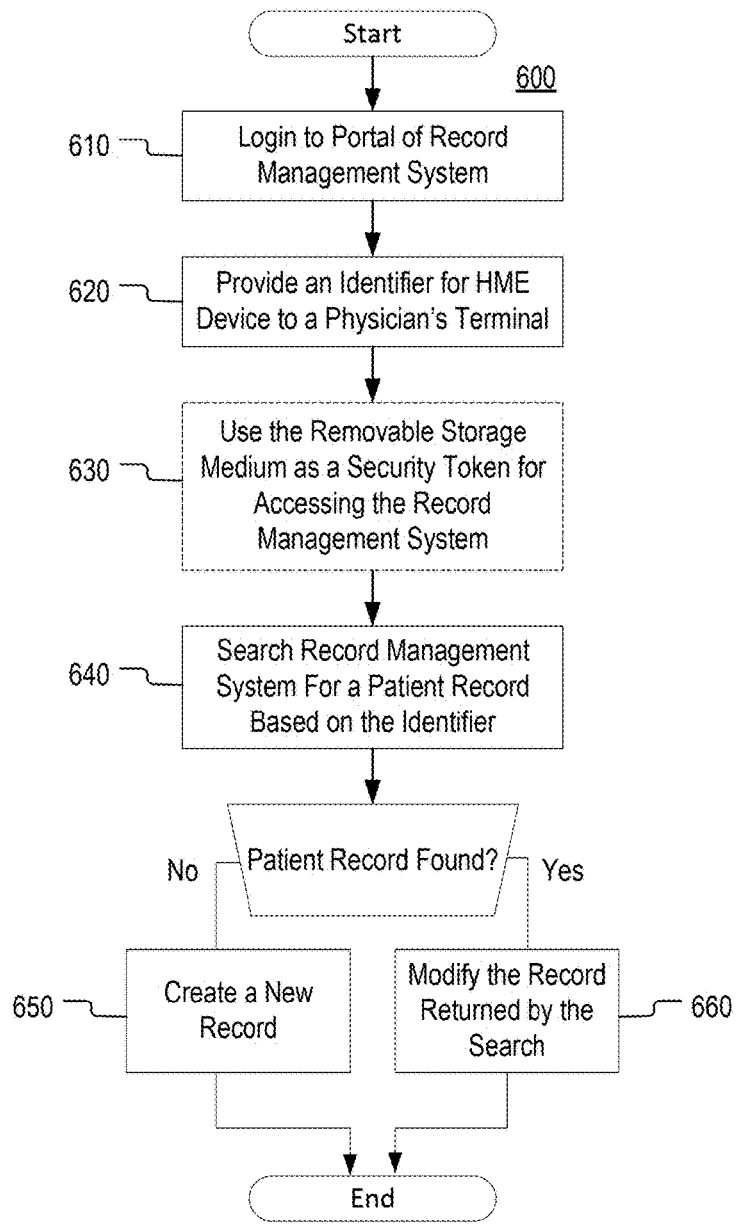

FIG. 12 depicts a flowchart of a process in accordance with aspects of the disclosure.

FIG. 13 depicts a flowchart of a process associated with the process of FIG. 12.

FIG. 14 depicts a flowchart of another process associated with the process of FIG. 12.

Figure 15:
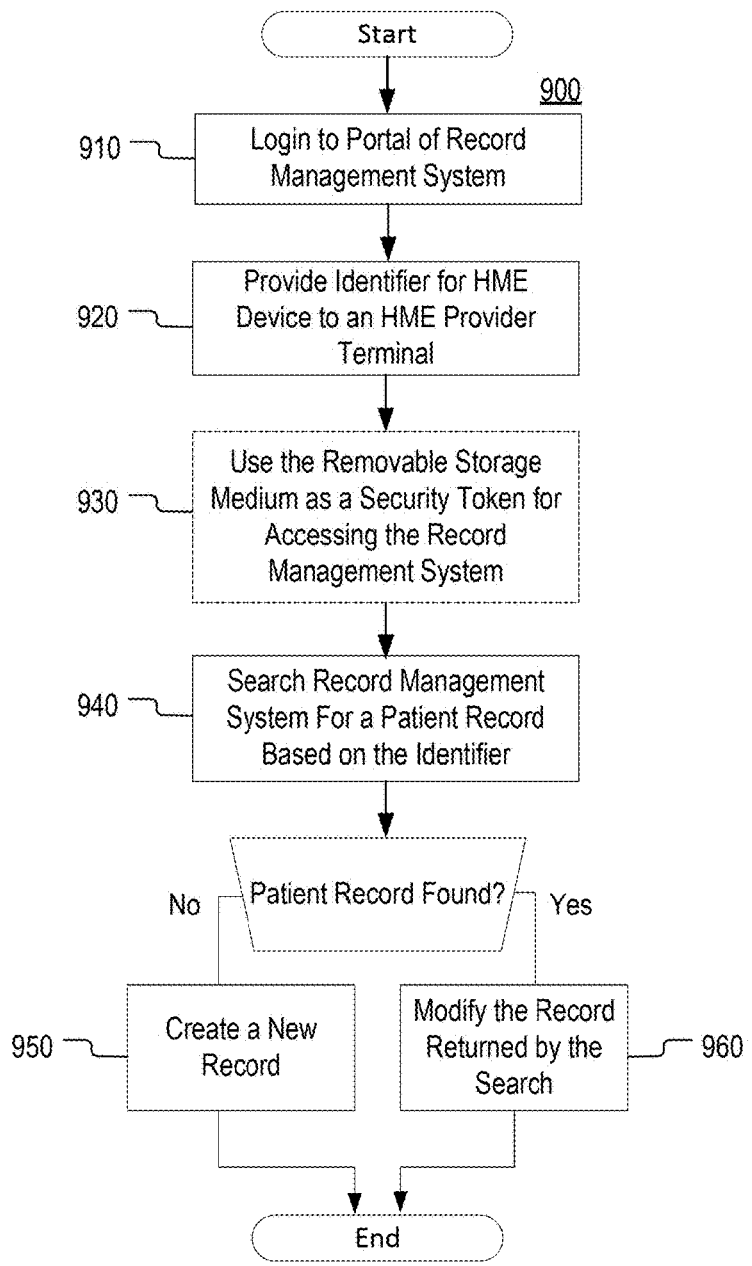

FIG. 15 depicts a flowchart of a process in accordance with aspects of the disclosure.

Figures 16, 17:
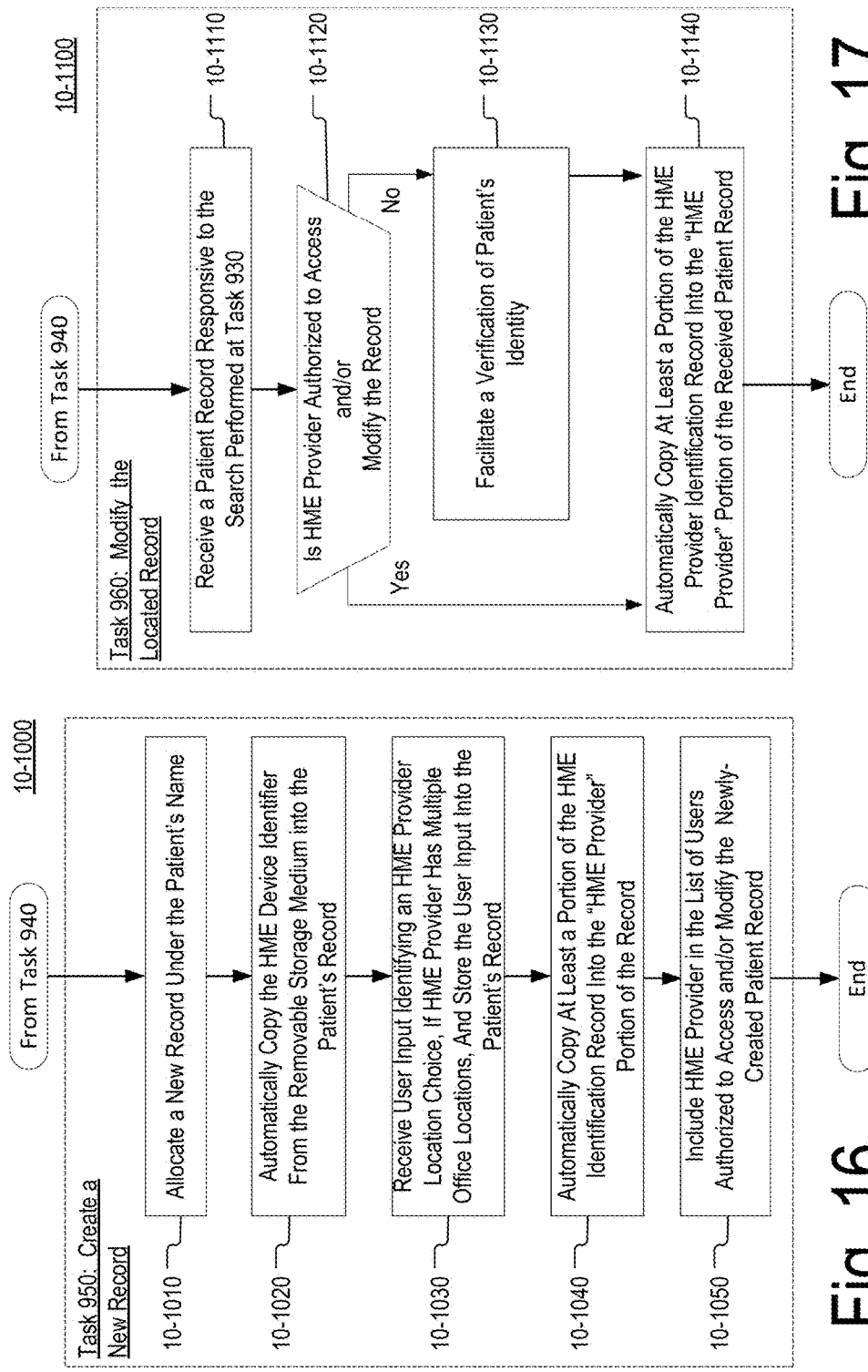

FIG. 16 depicts a flowchart of a process associated with the process of FIG. 15.

FIG. 17 depicts a flowchart of another process associated with the process of FIG. 15.

Figure 18A:
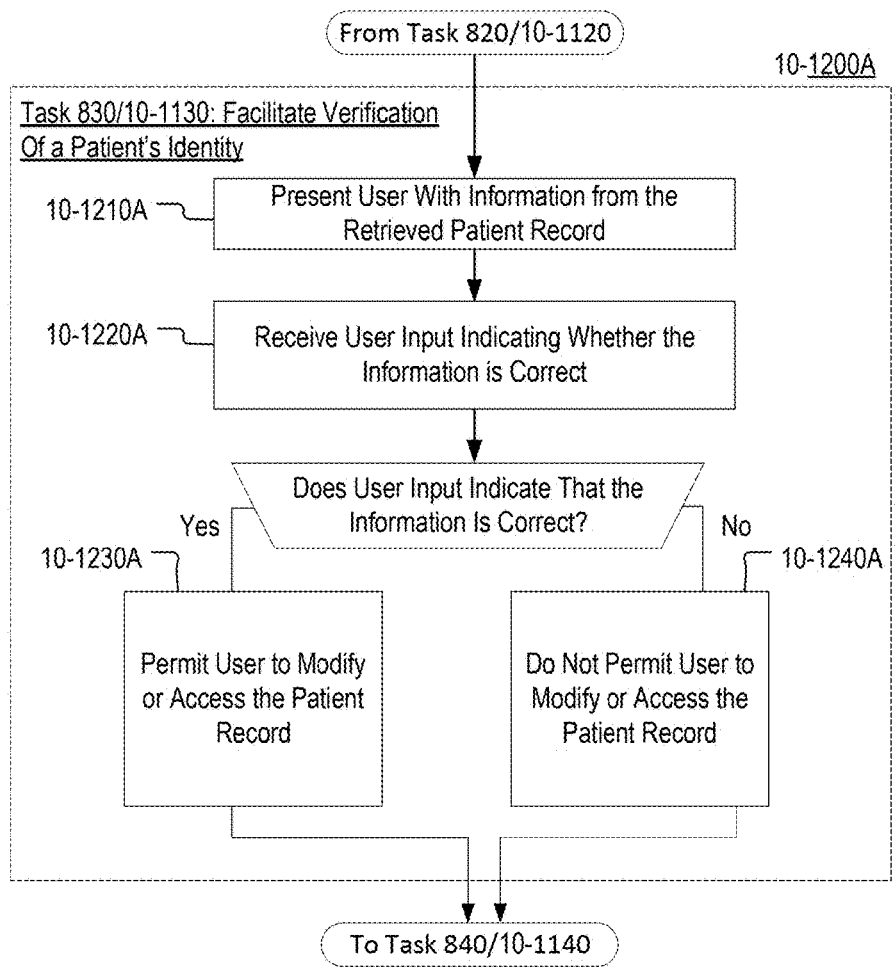

FIG. 18A depicts a flowchart of process associated with FIGS. 14 and 17.

Figure 18B:
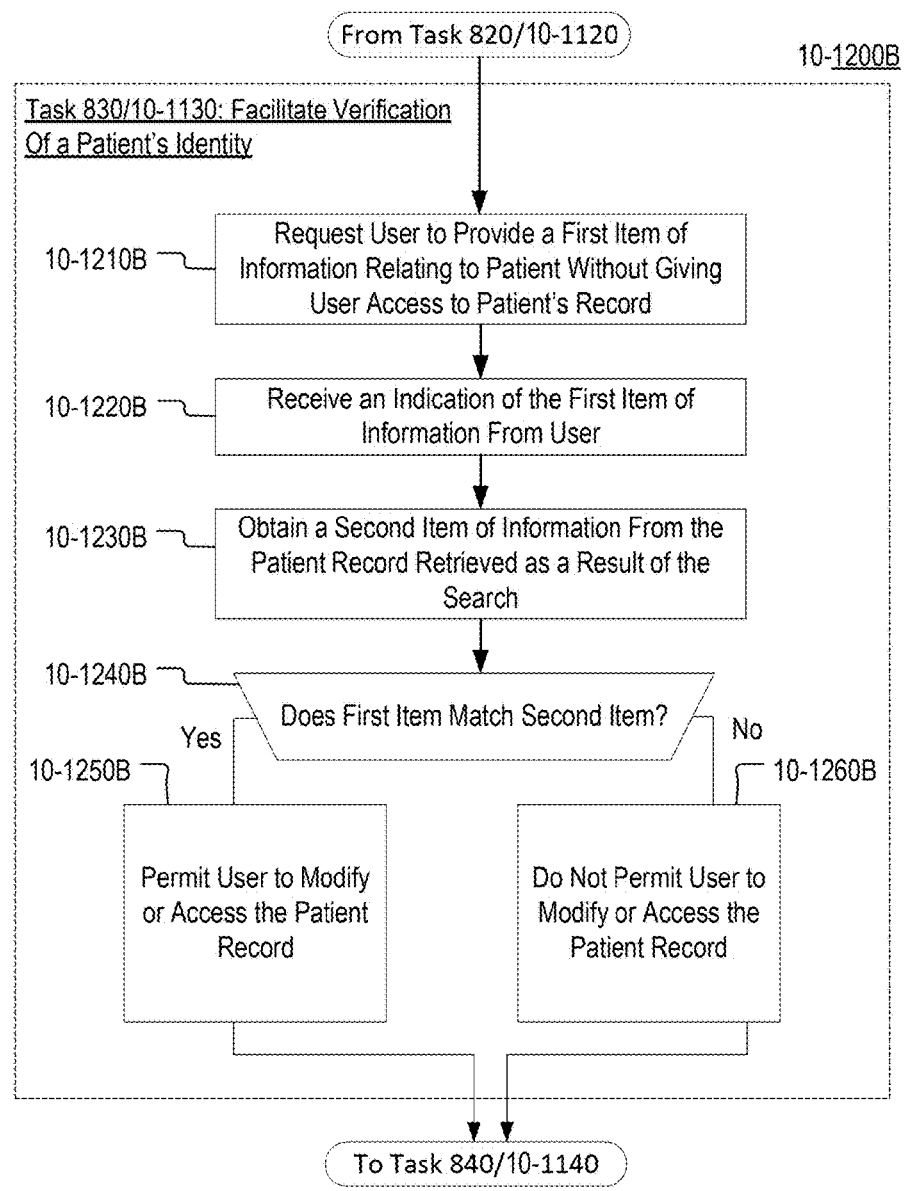

FIG. 18B depicts a flowchart of another process associated with FIGS. 14 and 17.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

4.1 Treatment Systems

In one form, the present technology may be incorporated within or in communication (wired or wireless) with apparatus for treating a respiratory disorder. The apparatus may comprise a flow generator or blower for supplying pressurised respiratory gas, such as air, to the patient 1000 via an air delivery tube leading to a patient interface 3000.

4.2 Therapy

In one form, the present technology comprises a method for treating a respiratory disorder comprising the step of applying or adjusting positive pressure to the entrance of the airways of a patient 1000. The treatment (e.g. positive pressure) may be any type such as a CPAP treatment, automatic titrating pressure (APAP), bi-level PAP or other suitable respiratory treatment.

4.2.1 Nasal CPAP for OSA

For example, in one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

In certain embodiments of the present technology, mouth breathing is limited, restricted or prevented.

4.3 Patient Interface 3000

A non-invasive patient interface 3000 in accordance with one aspect of the present technology may optionally include any one or more of the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange 3110 and a support flange 3120. Preferably the sealing flange 3110 comprises a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge 3220 of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged, to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement-both displacement and angular-of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Plenum Chamber 3200

Preferably the plenum chamber 3200 has a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

4.3.3 Positioning and Stabilising Structure 3300

Preferably the seal-forming structure 3100 of the patient interface 3000 of the present technology is held in sealing position in use by the positioning and stabilising structure 3300.

4.3.4 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3500, e.g. a swivel 3510.

4.3.5 Decoupling Structure(s) 3500

In one form the patient interface 3000 includes at least one decoupling structure 3500, for example a swivel 3510 or a ball and socket 3520.

4.3.6 Connection Port 3600

Connection port 3600 allows for connection to the air circuit 4170.

4.3.7 Forehead Support 3700

In one form, the patient interface 3000 includes a forehead support 3700.

4.3.8 Anti-Asphyxia 3800

In one form, the patient interface 3000 includes an anti-asphyxia valve 3800.

4.3.9 Ports 3900

In one form of the present technology, a patient interface 3000 includes one or more ports, that allow access to the volume within the plenum chamber 3200. In one form this allows a clinician to supply supplemental oxygen. In one form this allows for the direct measurement of a property of gases within the plenum chamber 3200, such as the pressure.

4.4 PAP Device 4000

An example PAP device 4000 in accordance with one aspect of the present technology may be formed with mechanical and pneumatic components 4100, electrical components 4200 and may be programmed to execute one or more algorithms 4300. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable pressure device 4140 capable of supplying air at positive pressure (preferably a blower 4142), and an outlet muffler 4124. One or more pressure sensors and flow sensors are included in the pneumatic path.

The preferred pneumatic block 4020 comprises a portion of the pneumatic path that is located within the external housing 4010.

The PAP device 4000 preferably has an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 is programmed to execute one or more algorithm 4300 modules, preferably including a pre-processing module 4310, a therapy engine module 4320, a pressure control module 4330, and further preferably a fault condition module 4340.

4.4.1 PAP Device Mechanical & Pneumatic Components 4100

4.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 4b.

In one form, an outlet air filter 4114, for example an antibacterial filter, is located between an outlet of the pneumatic block 4020 and a patient interface 3000. See FIG. 4b.

4.4.1.2 Muffler(s) 4120

In one form of the present technology, an inlet muffler 4122 is located in the pneumatic path upstream of a blower 4142. See FIG. 4b.

In one form of the present technology, an outlet muffler 4124 is located in the pneumatic path between the blower 4142 and a patient interface 3000. See FIG. 4b.

4.4.1.3 Pressure Device 4140

In an example form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 liters/minute, at a positive pressure in a range from about 4 cmH$_2$O to about 20 cmH$_2$O, or in other forms up to about 30 cmH$_2$O.

The pressure device 4140 may be under the control of the therapy device controller 4240.

4.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

4.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

4.4.1.6 Air Circuit 4170

An air circuit 4170 in accordance with an aspect of the present technology is constructed and arranged to allow a flow of air or breathable gasses between the pneumatic block 4020 and the patient interface 3000.

4.4.1.7 Oxygen Delivery

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

4.4.2 PAP Device Electrical Components 4200

4.4.2.1 Basic PAP Device

Some basic PAP devices, such as PAP device 4000, are essentially electromechanical devices that do not include processing capabilities.

4.4.2.1.1 Power Supply 4210

Power supply 4210 supplies power to the other components of the basic PAP device 4000: the input device 4220, the central controller 4230, the therapy device 4245, and the output device 4290.

In one form of the present technology, power supply 4210 is internal of the external housing 4010 of the PAP device 4000. In another form of the present technology, power supply 4210 is external of the external housing 4010 of the PAP device 4000.

4.4.2.1.2 Input Device(s) 4220

Input devices 4220 comprises buttons, switches or dials to allow a person to interact with the PAP device 4000. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

4.4.2.1.3 Central Controller 4230

In one form of the present technology, the central controller 4230 is a dedicated electronic circuit configured to receive input signal(s) from the input device 4220, and to provide output signal(s) to the output device 4290 and/or the therapy device 4245 controller.

In one form, the central controller 4230 is an application-specific integrated circuit. In another form, the central controller 4230 comprises discrete electronic components.

4.4.2.1.4 Therapy Device 4245

In one form of the present technology, the therapy device 4245 is configured to deliver therapy to a patient 1000 under the control of the central controller 4230. Preferably the therapy device 4245 is a positive air pressure device 4140.

4.4.2.1.5 Output Device 4290

An output device 4290 in accordance with the present technology may take the form of one or more of a visual, audio, and haptic output. A visual output may be a Liquid Crystal Display (LCD) or Light Emitting Diode (LED) display. An audio output may be a speaker or audio tone emitter.

4.4.2.2 Microprocessor-Controlled PAP Device

4.4.2.2.1 Power Supply 4210

In one form of the present technology power supply 4210 is internal of the external housing 4010 of the PAP device 4000. In another form of the present technology, power supply 4210 is external of them.

In one form of the present technology power supply 4210 provides electrical power to the PAP device 4000 only. In another form of the present technology, power supply 4210 provides electrical power to both PAP device 4000 and humidifier 5000.

4.4.2.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen.

The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

4.4.2.2.3 Central controller 4230

In one form of the present technology, the central controller 4230 is a processor suitable to control a PAP device 4000 such as an x86 INTEL processor.

A processor suitable to control a PAP device 4000 in accordance with another form of the present technology includes a processor based on ARM Cortex-M processor from ARM Holdings. For example, an STM32 series microcontroller from ST MICROELECTRONICS may be used.

Another processor suitable to control a PAP device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the processor for the PAP device 4000. For example a processor from the MSP430 family of microcontrollers, manufactured by TEXAS INSTRUMENTS, may be used.

The processor is configured to receive input signal(s) from one or more transducers 4270, and one or more input devices 4220.

The processor is configured to provide output signal(s) to one or more of an output device 4290, a therapy device controller 4240, a data communication interface 4280 and humidifier controller 5250.

The processor, or multiple such processors, is configured to implement the one or more methodologies described herein such as the one or more algorithms 4300 expressed as computer programs stored in a computer readable storage medium, such as memory 4260. In some cases, as previously discussed, such processor(s) may be integrated with a PAP device 4000. However, in some devices the processor(s) may be implemented discretely from the flow generation components of the PAP device, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

4.4.2.2.4 Clock 4232

Preferably PAP device 4000 includes a clock 4232 that is connected to processor:

4.4.2.2.5 Therapy Device Controller 4240

In one form of the present technology, therapy device controller 4240 is a pressure control module 4330 that forms part of the algorithms 4300 executed by the processor.

In one form of the present technology, therapy device controller 4240 is a dedicated motor control integrated circuit. For example, in one form a MC33035 brushless DC motor, controller, manufactured by ONSEMI is used.

4.4.2.2.6 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

4.4.2.2.7 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

In one form of the present technology, the memory 4260 acts as a computer readable storage medium on which is stored computer program instructions expressing the one or more methodologies described herein, such as the one or more algorithms 4300.

4.4.2.2.8 Transducers 4270

Transducers may be internal of the device, or external of the PAP device. External transducers may be located for example on or form part of the air delivery circuit, e.g. the patient interface. External transducers may be in the form of non-contact sensors such as a Doppler radar movement sensor that transmit or transfer data to the PAP device.

4.4.2.2.8.1 Flow

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element. Other flow sensors may be implemented such as a hot wire mass airflow sensor.

In use, a signal representing total flow Qt from the flow transducer 4274 is received by the processor.

4.4.2.2.8.2 Pressure

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the processor. In one form, the signal from the pressure transducer 4272 is filtered prior to being received by the processor.

4.4.2.2.83 Motor Speed

In one form of the present technology a motor speed signal 4276 is generated. A motor speed signal 4276 is preferably provided by therapy device controller 4240. Motor speed may, for example, be generated by a speed sensor, such as a Hall effect sensor.

4.4.2.2.9 Data Communication Systems 4280

In one preferred form of the present technology, a data communication interface 4280 is provided, and is connected to the processor. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of the processor. In another form, data communication interface 4280 is an integrated circuit that is separate from the processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

4.4.2.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.2.2.10.1 Display Driver 4292

A display driver 4292 receives as an input the characters, symbols, or images intended for display on the display 4294, and converts them to commands that cause the display 4294 to display those characters, symbols, or images.

4.4.2.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.4.3 PAP Device Algorithms 4300

4.4.3.1 Pre-Processing Module 4310

An pre-processing module 4310 in accordance with the present technology receives as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation algorithm 4312, vent flow algorithm 4314, leak flow algorithm 4316, respiratory flow algorithm 4318, and jamming detection algorithm 4319.

4.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

4.4.3.1.2 Vent Flow

In one form of the present technology, a vent flow algorithm 4314 receives as an input an estimated pressure, Pm, in the patient interface 3000 and estimates a vent flow of air, Qv, from a vent 3400 in a patient interface 3000.

4.4.3.1.3 Leak Flow

In one form of the present technology, a leak flow algorithm 4316 receives as an input a total flow, Qt, and a vent flow Qv, and provides as an output a leak flow Ql by calculating an average of Qt-Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered non-vent flow Qt-Qv, and low pass filtered square root of pressure Pm, where the low pass filter time constant has a value sufficiently long to include several breathing cycles, e.g. about 10 seconds.

4.4.3.1.4 Respiratory Flow 4318

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

4.4.3.2 Therapy Engine Module 4320

In one form of the present technology, a therapy engine module 4320 receives as inputs one or more of a pressure, Pm, in a patient interface 3000, and a respiratory flow of air to a patient, Qr, and provides as an output, one or more therapy parameters in a therapy parameter determination process 4329.

In one form of the present technology, a therapy parameter is a CPAP treatment pressure Pt.

In one form of the present technology, a therapy parameter is one or more of a level of pressure support, and a target ventilation.

4.4.3.2.1 Phase Determination

In one form of the present technology, the PAP device 4000 does not determine phase.

In one form of the present technology, a phase determination algorithm 4321 receives as an input a signal indicative of respiratory flow, Qr, and provides as an output a phase of a breathing cycle of a patient 1000.

In one form, the phase output is a discrete variable with values of either inhalation or exhalation.

In one form, the phase output is a discrete variable with values of one of inhalation, mid-inspiratory pause, and exhalation.

In one form, the phase output is a continuous variable, for example varying from 0 to 1, or 0 to 2Pi.

In one form, the phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

4.4.3.2.2 Waveform Determination

In one form of the present technology, a control module 4330 controls a therapy device 4245 to provide an approximately constant positive airway pressure throughout a respiratory, cycle of a patient.

In one form of the present technology, a control module 4330 controls a therapy device 4245 to provide positive airway pressure according to a predetermined waveform of pressure vs phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 receives as an input a value indicative of current patient ventilation, Vent, and provides as an output a waveform of pressure vs. phase.

4.4.3.2.3 Ventilation Determination 4323

In one form of the present technology, a ventilation determination algorithm 4323 receives an input a respiratory flow Qr, and determines a measure indicative of patient ventilation, Vent.

In one form ventilation determination algorithm 4323 determines a current value of patient ventilation, Vent, as the half the low-pass filtered absolute value of respiratory flow, Qr.

4.4.3.2.4 Determination of Inspiratory Flow Limitation

In one form of the present technology, a processor executes one or more algorithms for the detection of inspiratory flow limitation.

In one form the flow limitation algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6a. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by processor for the preceding several inspiratory events. This is repeated over the same inspiratory events for the second such point, and so on. Thus, for example, sixty five scaled data points are generated by processor; and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

4.4.3.2.5 Determination of Apneas and Hypopneas 4325

In one form of the present technology, a processor executes one or more algorithms for the determination of the presence of apneas and/or hypopneas.

Preferably the one or more algorithms receive as an input a respiratory flow signal Qr and provide as an output a flag that indicates that an apnea or respectively an hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow; for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for, example an RMS flow. The second flow threshold may be a relatively long-term measure of flow. The second flow threshold is greater than the flow threshold used to detect apneas.

4.4.3.2.6 Determination of Snore

In one form of the present technology, a processor executes one or more snore algorithms for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

4.4.3.2.7 Determination of Airway Patency

In one form of the present technology, a processor executes one or more algorithms for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency algorithm 4327 receives as an input a respiratory flow signal Qr, and determines the presence or absence of a cardiogenic signal. The absence of a cardiogenic signal is taken to be an indication of a closed airway.

4.4.3.2.8 Determination of Treatment Pressure

In one form of the present technology, a processor executes one or more algorithms for the determination of a target treatment pressure Pt.

For example, the therapy parameter determination process 4329 receives input such as one of more of the following:
  i. A measure of respiratory phase;
  ii. A waveform;
  iii. A measure of ventilation;
  iv. A measure of inspiratory flow limitation;
  v. A measure of the presence of apnea and/or hypopnea;
  vi. A measure of the presence of snore;
  vii. a sleep stage indication; and
  viii. A measure of the patency of the airway.

This processing may determine the treatment pressure Pt as a function of indices or measures of one or more of flow limitation, apnea, hypopnea, patency, sleep stage and snore and also may optionally rely on a target ventilation from a target ventilation determination process 4328. In one implementation, these measures are determined on a single breath basis, rather than on an aggregation of several previous breaths.

4.4.3.3 Control Module 4330

A control module 4330 in accordance with one aspect of the present technology receives as an input a target treatment pressure Pt, and controls a therapy device 4245 to deliver that pressure.

A control module 4330 in accordance with one aspect of the present technology receives as an input an EPAP pressure and an IPAP pressure, and controls a therapy device 4245 to deliver those respective pressures.

4.4.3.4 Detection of Fault Conditions 4340

In one form of the present technology, a processor executes one or more methods for the detection of fault conditions. Preferably the fault conditions detected by the one or more methods includes at least one of the following:
  Power failure (no power, or insufficient power)
  Transducer fault detection
  Failure to detect the presence of a component
  Operating parameters outside recommended ranges (e.g. pressure, flow, temperature, PaO$_2$)
  Failure of a test alarm to generate a detectable alarm signal.

Upon detection of the fault condition, the corresponding algorithm signals the presence of the fault by one or more of the following:
  Initiation of an audible, visual &/or kinetic (e.g. vibrating) alarm
  Sending a message to an external device
  Logging of the incident

4.4.3.5 Therapy Device 4245

In a preferred form of the present technology, the therapy device 4245 is under the control of the control module 4330 to deliver therapy to a patient 1000.

Preferably the therapy device 4245 is a positive air pressure device 4140.

4.5 Humidifier 5000

4.5.1 Humidifier

In one form of the present technology there is provided a humidifier 5000 which may typically include a water reservoir and a heating plate.

4.6 Serial Number Identification

FIG. 7 depicts a schematic diagram of a patient records management system 100. As illustrated, the patient records management system 100 includes a records management system 110 for storing one or more records relating to the use of an HME device 130 by a patient 120. The records management system 110 may provide a centralized database that enables the accessing of the patient's (120) records over a communication network 160. The records management system 110 may further be configured to process the patient's records and generate at-a-glance compliance reports for the patient. The records management system 110, in one example may be ResMed's EASYCARE ONLINE™ system, but it may also be any type of patient record management system. The records management system 110 may include one or more database servers, as well as any other equipment that is commonly found in record management systems (e.g., NAS drives, UPS devices, network switches, or gateways).

HME device 130 may be a respiratory treatment device, such as a continuous positive air pressure (CPAP) device. The HME device 130 may include a processor and a removable medium drive (or port) for accepting a removable storage medium 170. The removable storage medium 170 may be an SD card, but in other examples it may be a USB drive, mini-CD, DVD, or any other type of removable storage medium. In yet other examples, the removable storage medium may be an RFID card, a Bluetooth enabled token, or any other token having short-range wireless capabilities.

Physician terminal 140 may be a processor-based device located at various physician premises, such as a hospital, clinic, or office. The physician terminal may be a computer, smart phone, a tablet, or another processor based device. The physician terminal 140 may be associated with a physician that is in charge of the treatment of the patient 120 with the HME device 130. Alternatively, the terminal 140 may belong to a physician, whose office the patient incidentally visits, e.g., on the way to work.

HME provider terminal 150 may be a device located at the premises of an HME provider. The HME provider terminal may be a processor-based device, such as a computer, smart phone, a tablet, or another processor based device. The HME provider terminal 150 may be associated with an HME provider in charge of dispensing the HME device 130 to the patient 120. Both the physician terminal 140 and the HME provider terminal 150 may be connected to the records management system 110 via a communications network 160. In this example, the network 160 is the Internet, but in other examples the network 160 may be another type of switched or non-switched network (e.g. ATM, TCP/IP etc.)

The removable storage medium 170 may store an identifier for the HME device, compliance data, and prescription data. Data stored on the removable storage medium 170 may be uploaded to the records management system 110 and stored into one or more electronic records associated with the patient 120. The data may be uploaded by either one of the physician terminal 140 and the HME provider terminal 150. More particularly, either one of the terminals 140 and 150 may retrieve data from the removable storage medium 170 and transmit the retrieved data, over the network, 160, to records management system 110 for storage in a record associated with the patient 120.

Although in this example a removable storage medium is used to store the identifier for the HME device 130, as well as other data, in other examples non-removable memory may be used to store this information, such as RAM or an SSD drive that is part of the HME device. Furthermore, although in this example data stored in the HME device 130 is communicated to the terminals 140 and 150 by physically placing the storage medium 170 into a reader device (or port) on the terminals, in other examples the data, including the device identification number, may be communicated via a wireless connection, such as Bluetooth, Wireless USB, WiFi, GSM or GPRS.

FIG. 8 depicts a schematic diagram of hardware devices of the patient records management system 100 in accordance with another aspect of the disclosure. According to this example, the records management system 110 may include at least a server 200. The server 200 may include a processor 210 and memory 220. Memory 220 may store information accessible by processor 210, including executable code 240 that may be executed by the processor 210. The memory also includes data 230 that may be retrieved, manipulated or stored by the processor. The memory may be of any type of non-transitory tangible media capable of storing information accessible by the processor, such as a hard-drive, memory card, ROM, RAM, DVD, CD-ROM, write-capable, and read-only memories. The processor 210 may be any well-known processor, such as commercially available processors or any of the processing circuits described in more detail throughout this specification. Alternatively, the processor may be a dedicated controller such as an ASIC.

Data 230 may be retrieved, stored or modified by processor 210 in accordance with the executable code 240. For instance, although the system and method are not limited by any particular data structure, the data may be stored in computer registers, in a relational database as a table having a plurality of different fields and records, or XML documents. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

The data 230 may include compliance data record 232 and patient record 234. The compliance data record 232 may include information related to the usage of the HME device 130 by the patient 120, such as information identifying time periods during which the HME device 130 is used; detected respiratory events; sensor data obtained by the HME device 130, which can include leak events, minute ventilation, tidal volume and respiratory rate; as well as information relating to various settings of the HME device.

The patient record 234 may include one or more data records configured to store any type of information related to the treatment of the patient 120 with the HME device 130. Each data record may be a file, a database data structure, or any other type of data structure. As illustrated in FIG. 9, the patient record 234 may include one or more of a "patient information" portion 310, a "physician information" portion 320, an "HME device information" portion 330, an "HME provider information" portion 340, and a permissions structure 350.

The "patient information" portion 310 may include information relating to the patient 120, such as a name, address, age, gender, weight, height, diagnosis, prescription, or any other information that is commonly found in medical records. The "physician information" portion 320 may include information relating to one or more physicians that are associated with the patient 120. For each physician, the portion 320 may include a name, address, license number, or any other type of physician information that is commonly kept in medical records.

The "HME device information" portion 330 may include information relating to an HME device that has been assigned to the patient 120. In this example, the portion 320 may include an identifier for the HME device 130 (e.g., HME device identifier), model number, make, firmware version, software version or any other similar information. Notably, the identifier stored in the portion 330 may be a copy of the identifier 174 that is stored on the removable storage medium 170. The "HME provider information" portion 340 may include information to an HME provider that has dispensed the HME device 130. The information may include an identifier for the HME Provider (e.g., company name), address, inventory number for the HME device 130, details of the specific HME that works with the patient, or any other similar information. The permission structure 350 may identify one or more users (e.g., physicians, HME providers, payers, etc.) that are permitted to access, modify, and/or share the patient record 234. The permission structure 350 may be an alphanumerical string, bit string, a text file, a list or another data structure. Depending on predetermined arrangements, some of the users may have a limited access to the patient's data, including only the ability to view the data or to only to upload new data. Other users may be given full access to the patient's data, including editing the data. In this example, the permission structure 350 may associate user log-in names with specific permission sets. In instances, where the user log-in names are entity-wide (e.g., one user name for a whole hospital, clinic, or HME provider) the same permission sets may be granted to all users who log using the same credential.

Returning to FIG. 8, in one aspect, the executable code 240 may include an online portal 242 for accessing the records management system 110. The online portal 242 may interact with the physician terminal 140 or HME provider terminal 150 to provide access to patient records that are stored in the records management system 110. More specifically, the online portal may include software (e.g., web-services software) for receiving and executing requests that are transmitted by the terminals 140 and 150 over the network 160. Such requests may be search requests or requests to create, access, modify, or share patient records.

In another aspect, the executable code 240 may include database server software, such as an SQL server, that is configured to receive instructions, over the network 160, to retrieve or store data into the patient record 234. The instructions may be transmitted by the physician terminal 140 and/or the HME provider terminal 150. To that end, the compliance data record 232 and patient record 234 may be implemented as database data structures, such as tables, records, columns, rows.

According to another aspect, the executable code 240 may include software for processing the compliance data record 232 and generating reports based on the record. The generated reports may be compliance reports, such as the report 410 that is depicted in FIG. 10. As illustrated, the reports may identify times at which the patient was using the HME device 130, the manner in which the HME device 130 is used, or any other type of information related to the usage of the HME device 130.

According to yet another aspect, the executable code 240 may include an HTTP server for providing users with a webpage for accessing and interacting with the records management system 110. In instances where the application 250 is implemented as a Java® applet, the web server may transmit (e.g., serve) the applet to the terminals 140 and 150 when a user of the terminals has logged in. Once it is started and running on one of the physician terminal 140 and HME provider terminal 150, the Java® applet may start interacting with the online portal 242 to create, access, modify, or share patient records that are stored by the records management system 110.

The removable storage medium 170 may store device information 172 and compliance data 176. The device information 172 may include a model number for the HME device 130, make of the HME device 130, firmware version, or any other similar information related to the HME device. In some instances, the device information 172 may include an HME device identifier 174. The HME device identifier 174 may be number, string, alphanumerical string, or another object that is capable of distinguishing the HME device from one or more other HME devices. In one aspect, the HME device identifier 174 may be unique for the records management system 110, such as an identifier that can be entered only once into the records management system 110 and be associated with only one HME device. In another aspect, the HME device identifier 174 may be the HME device's manufacturer's serial number, the removable storage medium's 170 manufacturer's serial number, or any other type of information.

In one aspect, the HME device identifier 174 may be recorded on the removable storage medium 170 by the HME device 130 (e.g., by using a reader/writer that is built into the HME device 130). Alternatively, the HME device identifier 174 may be recorded onto the removable storage medium 170 by a physician, HME provider, or the manufacturer of the HME device 130. In yet another example, the HME device identifier 174 may be engraved or encoded on an external surface of a component of the HME device, such as the removable storage medium 170 such that it may be read by a scanning device (such as reader device 143, reader device 153, or any other scanning device). In this way, the HME device identifier 174 may be encoded or engraved as a bar code, such as a two-dimensional, three-dimensional, QR code, or any other machine readable code. In still another example, the HME device identifier may not be stored on a removable storage medium, but may be encoded or engraved on a tag that may be attached to the HME device or the patient, such that the tag may be read by the scanning device. In still other aspects, the tag may be an RFID enabled. ID tag that may be stored on the patient's person, such as in a wallet or a pocket. In this way, the patient need not be required to remove the RFID tag from their wallet or pocket in order to transmit the HME identifier, but need only be within RFID communication distance. In instances where the HME device identifier 174 is a manufacturer's serial number for the HME device 130, the HME device identifier 174 may be generated in the manner manufacturer serial numbers are normally generated. In other instances, however, where the HME device identifier 174 is not a manufacturer's serial number, the HME device identifier 174 may be generated by the records management system 110 and provided to the HME device, the HME device's 130 manufacturer, a physician, or an HME provider for recording onto the removable storage medium 170. In such instances, the HME device identifier 174 may be any type of string, number, or object that is capable of distinguishing the HME device 130 from the HME device identifiers for other HME devices that are associated with records stored in the records management system 110. The HME device identifier 174 may be distributed by the records management system 110 over the network 160. Although in this example the records management system 110 acts as the issuing authority for the HME device identifier 174, in other examples the issuing authority may be Separate from the records management system 110.

The physician terminal 140 may include a memory 141, a reader device 143, and a processor 144. The memory 141 may include at least one of volatile memory (e.g., RAM) and non-volatile memory (e.g., SSD, flash, hard drive. The reader device 143 may be an SD card reader, CD-ROM reader, RFID receiver, Bluetooth receiver, a short range wireless receiver, a USB port, a Serial Port, an SATA port, or any another device that may be used to read information from the removable storage medium. The processor 144 may be any type of special-purpose or general-purpose processor, such as FPGA, x86, or MIPS. The processor 144 may be coupled to both the memory 141 and the reader device 143.

As illustrated, the physician terminal 140 may store in the memory 141 a physician information record 142. The physician information record 142 may be a file, database data structure, or any other type of data structure that stores information about the physician associated with the physician terminal 140. As discussed above with respect to the "physician information" portion 320, the information stored in the physician information record 142 may include a name, address, license number, or any other type of physician information that is commonly kept in medical records.

The HME provider terminal 150 may include a memory 151, a reader device 153, and a processor 154. The memory 151 may include at least one of volatile memory (e.g., RAM) and non-volatile memory (e.g., SSD, flash, hard drive. The reader device 153 may be an SD card reader, CD-ROM reader, RFID receiver, Bluetooth receiver, a short range wireless receiver, a USB port, a Serial Port, an SATA port, or any another device that may be used to read information from the removable storage medium. The processor 154 may be any type of special-purpose or general-purpose processor, such as FPGA, x86, or MIPS. The processor 154 may be coupled to both the memory 151 and the reader device 153.

The HME provider terminal 150 may store in the memory 151, an HME identification record 152. The HME provider identification record 152 may be a file, database data structure, or any other type of data structure that stores information about the HME provider associated with the HME provider terminal 150. As discussed above with respect to the "HME provider information" portion 340, the information stored in the record 152 may include an identifier for the HME Provider (e.g., company name), address, or any other similar information.

Both the physician terminal 140 and the HME provider terminal 150 may execute instances of a record management application 250. The record management application may include software for storing and retrieving information from the patient record 234. For example, the record management application 250 may be browser-based (e.g., a Java® applet), standalone, or any other type of application. When executed on the physician terminal 140, the application 250 may be configured to perform, at least in part, the process 600 discussed with respect to FIG. 6. When executed on the HME provider terminal 150, the application 250 may be configured to perform, at least in part, the process 900 discussed with respect to FIG. 9. Although the terminals 140 and 150 execute different instances of the same software, in other examples the terminals 140 and 150 may execute different software applications.

The record management application 250 may provide users with an interface 500 for associating the HME device 130 with the patient record 234. As illustrated in FIG. 11, the interface 500 may include interface components 510-540 and a button 550. Each one of the interface components 510-540 may be a text input field, a text output field, or any other type of user interface component for inputting and/or outputting information (e.g., text or bitmap data). The interface component 510 may display information that has been retrieved from the portable removable storage medium 170 by the terminal executing the application 250 (e.g. physician terminal 140 or HME provider terminal 150). More particularly, the interface component 510 may display at least some of the device information 172 (data), including, but not limited to, the identifier 174.

The interface component 520 may be an input field for entering patient information. Alternatively, the interface component 520 may be an output field for displaying patient information that has been retrieved from the patient record 234. The interface component 530 may be an input field for entering physician information. Alternatively, the interface component 530 may be an output field for displaying patient information that has been retrieved from the "physician information" portion 320 of the patient record 234. As yet another alternative, the component 530 may be an output field for displaying information that is stored in the physician information record 142.

The interface component 540 may be an input field for entering HME provider information. Alternatively, the interface component 540 may be an output field for displaying HME information that has been retrieved from the "HME provider record" of patient record 234. As yet another alternative, the interface component 540 may be an output field for displaying information that is stored in the HME provider information record 152. The upload button 550 may be a button that triggers the upload and storage into the patient record 234 of at least some of the information displayed by any one of the interface components 510-540. For example, pressing the button 550 may result in uploading and storing of the identifier 174 that has been copied from the removable storage medium 170.

FIG. 12 depicts a flowchart of a process 600 related to the association of the HME device 130 with a patient record. The process of association is essentially the same, regardless of whether it is performed at the physician terminal 140 or an HME provider terminal 150. (FIG. 15 depicts an analogous process performed at an HME provider terminal 150.) At task 610, a user logs on to the records management system 110 by using the physician terminal 140. The user may be an agent of an entity, such as a hospital, clinic, hospital chain, HME provider organization, or a physician organization. In this example, the user is a physician. In one aspect, when logging in, the user may be authenticated using a credential, such as a log-in name, password and/or a security certificate. The credential may belong to an entity that the user is an agent of (e.g., the physician's own practice, clinic or hospital). Alternatively, the credential may be personal to the user. After the log in is completed, a user session is initiated at the records management system 110 for the user.

At task 620, the HME device identifier 174 is received by the physician terminal 140. The identifier may be provided to the system by inserting the removable storage medium 170 into a reader (or port) on the physician terminal 140 or an HME provider terminal 150. Alternatively, the identifier may be entered manually or even transmitted by the HME device by using a wireless or wired connection (e.g., Bluetooth or USB, GSM, GPRS, RFID, NFC, Bluetooth low energy (BLE), WIFI, etc.), or may be received from a scanning device. In either instance, the physician terminal 140 (or the HME provider terminal 150) may retrieve the HME device identifier without requiring the user to type it.

In other examples, a scanner, such as a barcode scanner, may scan a surface (e.g., external) of a component of the HME device such as the removable storage medium 170, to ascertain the HME device identifier 174, which may be engraved or encoded on a surface of the removable storage medium. In yet another example, the HME device identifier 174 may be retrieved by scanning a tag with the HME device identifier 174 encoded or engraved thereon, or the HME identifier may be transmitted from an RFID tag that may be stored on the patient's person or with the HME device.

At task 630, an authentication may be performed that utilizes the removable storage medium 170 (and/or more particularly the HME device identifier stored on the removable storage medium 170) as a security token or a password for accessing or modifying at least one of the records stored on the records management system 110. In some instances, the patient records management system 100 may permit the physician terminal 140 to perform the tasks 640-660 (discussed below) only if the physician terminal 140 and the removable storage medium 170 are collocated. A collocation may be considered to exist when the removable storage medium 170 is inserted into, or is otherwise reachable (e.g., via a short-range wireless connection, such as Bluetooth or RFID) by reader device 143 of the physician terminal 140).

Put differently, in some instances, the user may be required to be in physical possession of the removable storage medium 170 before one or more of the tasks 640-660 are executed. This feature may be useful in situations where a credential of a large organization (e.g., hospital or hospital chain) is used to log-in at task 610 and accesses to records associated with a given HME device is wanted to be restricted only to select few of the organization's employees (or agents). Notably, according to this example, the same removable storage medium that is used by the HME device 130 to collect compliance data may also be used as a hardware security token by (healthcare) entities, such as hospitals, physician practices, or HME providers. Thus, the entities may use the removable storage medium 170 to gain authorization to create, access, modify, or share records in the records management system 110 that are associated with the HME device 130.

In other instances, however, collocation between the removable storage medium 170 and the physician terminal 140 may not be required for the execution of the process 600 to proceed. In such instances, the HME device identifier obtained at task 620 may be used as a software token without the physical location of the removable storage medium 170 being accorded any significance. In either instance, however, at task 630, the HME device identifier received at task 620 may be validated and only upon a positive validation may the execution of at least one of tasks 640-660 be permitted to proceed.

In one aspect, the validation may include transmitting the identifier to a remote server (e.g., server 200) and receiving a response from the remote server that includes information about an HME device that is associated with the identifier. For example, the response may include information indicating the make, model number, and/or serial number of the associated HME device. The information from the response may be compared to information stored on the removable storage medium 170 and if there is a match, the serial number may be considered valid. In another aspect, the validation may include computing a hash code of the identifier, or using another similar approach, to ensure that the identifier retrieved from the removable storage medium 170 has not been corrupted. In yet another aspect, the validation may include ascertaining that the HME device identifier possesses a property that is known (or required) to be possessed by all valid HME device identifiers. In some instances, the execution of the process 600 may proceed to task 630 only if the identifier provided at task 610 is successfully validated.

At task 640, the physician terminal 140 searches the records management system 110 for a patient record associated with the HME device identifier 174. The search may involve submitting a search query to the server 200 with the search key being at least partially based on the HME device identifier 174 (e.g., the identifier 174 being used as a search key). In some instances, the search query may be generated automatically by the physician terminal 140, without the terminal's user having to manually type the HME device identifier 174 or the query itself. In some instances, the terminal 140 may transmit the search query only if the terminal 140 is collocated with the removable storage medium.

If the search fails to return a patient record associated with the HME device identifier, task 650 is executed and a new record is created and associated with the HME device 130. Alternatively, a search may be performed based on the patient's name and manually assign a device to the respective patient record. Otherwise, if the search returns a patient record, at task 660, the returned record is modified to identify, depending on the entity providing the memory device and the identification number, either the physician associated with the physician terminal 140 or the HME associated with the respective HME provider terminal 150. This identification is also referred to as an association. Whilst such as automatic association of the patient's record with the entity providing the HME device identifier can be effected during or after providing access or editing rights to the entity, it is best if it is effected before the provision of such an access. After a physician or an HME is associated with the patient record, they have access to it and can view and/or edit the record.

FIG. 13 depicts a flowchart of a process 700 associated with the creation of a new record for the patient 120 and associating that record with: (1) an HME device and (2) a physician (or another entity) in charge of a patient's treatment with the HME device. The process 700 may be executed, e.g. at step 650 of the process 600, in situations where a patient has already visited an HME, however no patient record has been created on the record management system at the time when later the patient visits the physician's office. As discussed above, the physician may first log onto the record management system, and perform a search based on the HME device identifier that is stored on the removable storage device. The records management system may receive the identification number of the HME device and check if the number is already registered to one of the patient records that are stored in the records management system 110. As in this example no such a record has been previously created by the HME provider, the physician has to create a new patient record in the record management system. Process 700 provides the details of the process of creating such a new record.

At task 710, a new record is allocated under the patient's name. In one aspect, the allocation may include the physician terminal 140 transmitting, over the network 160, a query (e.g., a database query or another type of query) to the server 200 instructing it to create a new patient record under the name of the patient 120. The query may include the patient's name or any other type of patient information as a parameter.

At task 720, the HME device identifier 174 is copied automatically from the removable storage medium 170 to the newly-created patient record. The automatic copying of the HME device identifier 174 removes the need for an operator to manually type the device identifier, and thus eliminates the possibility of a typographical error being introduced when the HME device identifier 174 is copied. The copying may include the physician terminal 140 transmitting, over the network 160, a query to the server 200 instructing it to store the HME device identifier into the newly-created patient record. The HME device identifier 174 may be transmitted as part of the query.

At task 730, the physician terminal 140 receives a user input identifying a preferred physician location and stores an indication of the preferred location into the patient record. The indication may be stored by transmitting a query, over the network 160, from the physician terminal 140 to the server 200. Task 730 may be executed only when there are multiple physician locations identified in the physician information record 142 that is stored on the physician terminal 140. Alternatively, instead of receiving a manually entered user input, the system may be arranged to automatically detect and record the location choice, based on information associated with a location of the physician terminal 140 or a server associated with the physician terminal 140.

At task 740, at least a part of the physician information record 142 is automatically copied into the patient record. The copied information may include physician name, address, license number, telephone number, or any other type of physician information that is normally kept in medical records. The information may be stored into the patient record by transmitting a query, over the network 160, from the physician terminal 140 to the server 200. The automatic copying of physician information removes the need for an operator to enter physician's information manually every time a patient is associated with an HME device.

At task 750, permissions structure 350 is modified to permit the physician associated with the physician's terminal 140 to access, modify, or share the newly-created patient's file. Thus, the physician is automatically associated with the patient's record and obtains certain rights to access and/or edit data in the record.

FIG. 14 depicts a flowchart of a process 800 associated with the updating of a record associated with the HME device 130 to include information about the physician in charge of the patient's 120 treatment. The process 800 may be executed, e.g. at step 660 of the process 600, in situations where a patient visits the physician's office after an HME provider has created a patient record in a database of the records management system 110 and associated that record with the HME device, identifier 174. Generally, access is granted to a medical entity (a physician or an HME) who is in possession of the SD card and, therefore, in possession of the device identification number. In this sense the identification number on the SD card is the key for accessing the patient record.

At task 810, a database record is retrieved responsive to the search performed at task 630. In this example, the physician terminal 140 receives a handle (or identifier) for a patient record in the records management system 110 that is associated with the provided HME device identifier 174. In other examples, however, the physician terminal 140 may receive a copy of the identified record.

At task 820, a determination is made whether the user that is logged on (e.g., the physician associated with the physician terminal 140) is permitted to modify the retrieved record. If the physician is already associated with the patient record by the HME or another entity, the physician is permitted to modify the retrieved record. The determination may be made, for example, based on (i) a permissions structure, such as the structure 350 and (ii) a log-in name (or another credential) used by the physician to log-in at task 610. If the physician is pre-authorized to modify the retrieved patient file, task 840 may be executed. Otherwise the execution of the process 800 proceeds to task 830, where the physician verifies the patient's identity to ensure that the retrieved record is for the same patient that is being treated by the physician.

At task 830, it is determined whether the retrieved record belongs to the patient 120 (e.g., the patient that provided the removable storage medium 170 to a physician or a HME provider). Upon finding a match, the server 200 modifies the permissions structure associated with the retrieved patient record to permit the user associated with the physician terminal 140 to access, share, and/or modify the retrieved data object. If a match is not found, the user is refused permission to modify the retrieved patient record and the process 800 terminates.

At task 840, at least a part of the physician information record 142 is automatically copied into the patient, record. The copied information may include physician name, address, license number, telephone number, or any other type of physician information that is normally kept in medical records. The information may be stored into the patient record by transmitting a query, over the network 160, from the physician terminal 140 to the server 200. Task 840 may be executed only if the physician associated with the physician terminal 140 is permitted to modify the retrieved data structure.

FIG. 15, depicts a flowchart of a process 900 related the association of the HME device 130 with a patient record. As mentioned in relation to FIG. 12, the process of association is the essentially the same, regardless of whether it is performed at the physician terminal 140 or an HME provider terminal 150.

At task 910 a representative of an HME provider (e.g., HME provider employee) logs onto the records management system 110. At task 920, the HME device identifier 174 is received by the HME provider terminal 150. The identifier may be provided by physically removing the removable storage medium 170 from the HME device 130 and inserting it into a reader (or port) on the HME provider terminal 150. Alternatively, the identifier may be transmitted by the HME device to the HME provider terminal by using a wireless or wired connection (e.g., Bluetooth or USB).

At task 930, an authentication is performed that utilizes the removable storage medium 170 (and/or the HME device identifier 174 stored on the removable storage medium 170) as a security token for accessing the records management system 110. Task 930 is identical to task 630. At task 940, the HME provider terminal 150 searches the records management system 110 for a patient record associated with the HME device identifier 174. The search may involve submitting a search query to the server 200 with the search key being at least partially based on the HME device identifier 174. In some instances, the search query may be generated automatically by the HME provider terminal 150 without the terminal's user having to manually type the HME device identifier 174 or the search query. If the search fails to return a patient record associated with the HME device identifier, task 950 is executed and a new record is created for the patient 120. Otherwise, if the search returns a patient record, at task 960, the returned record is modified to identify, depending on the entity providing the memory device and the identification number, either the physician associated with the physician terminal 140 or the HME associated with the respective HME provider terminal 150. This identification is also referred to as an association. After a physician or an HME is associated with the patient record, they have access to it and can view and/or edit the record.

FIG. 16 depicts a flowchart of a process 10-1000 associated with the creation of a new record for the patient 120 and associating that record with: (1) the HME device 130 and (2) an HME provider dispensing the HME device 130. The process 10-1000 may be executed, e.g. at step 950 of the process 900, in situations where a patient visits HME provider prior to visiting a physician's office to obtain guidance on how to use the device.

At task 10-1010, a new record is allocated under the patient's name. In one aspect, the allocation may include the HME provider terminal 150 transmitting, over the network 160, a query to the server 200 instructing it to create a new patient record under the name of the patient 120. The query may include the patient's name or any other type of patient information.

At task 10-1020, the HME device identifier 174 is automatically copied from the removable storage medium 170 to the patient record. The automatic copying dispenses with the need to manually type the device identifier into the HME provider terminal 150, and thus eliminates the possibility of a typographical error being introduced.

At task 10-1030, the HME provider terminal 150 receives a user input identifying a preferred HME provider location and stores an indication of the preferred location into the newly-created patient record. The indication may be stored by transmitting a query, over the network 160, from the HME provider terminal 150 to the server 200 instructing the server 200 to store the preferred location into the patient record. Task 10-1030 may be executed only when HME provider locations are identified in the HME provider information record 152. Alternatively, instead of receiving a manually entered user input, the system may be arranged to automatically detect and record the location choice, based on information associated with a location of the HME provider terminal 150 or a server associated with the HME provider terminal 150.

At task 10-1040, at least a part of the HME provider information record 152 is automatically copied into the patient record. The copied information may include, an identifier for the HME Provider (e.g., company name), address, or any other similar information. The information may be stored into the patient record by transmitting a query, over the network 160, from the HME provider terminal to the server 200. The automatic copying of physician information dispenses with the need for an operator to enter the HME provider's information manually every time a patient is associated with an HME device.

At task 10-1050, permissions structure 350 is modified to permit the HME provider associated with the HME provider terminal 150 to access, modify, or share the newly-created patient's file. Thus, the HME provider is automatically associated with the patient's record and obtains certain rights to access and/or edit data in the record.

FIG. 17 depicts a flowchart of a process 10-1100 associated with the updating of a record associated with the HME device 130 to include information about the HME provider dispensing the device. The process 10-1100 may be executed, e.g. at step 960 of the process 900, in situations where a patient visits the HME provider's office after a physician has created a patient record in the records management system 110 and associated that record with the HME device.

At task 10-1110, a database record is retrieved responsive to the search performed at task 930. In this example, the HME provider terminal 150 receives a handle (or identifier) for a patient record in the records management system 110 that is associated with the HME device identifier 174. In other examples, however, the HME provider terminal may receive a copy of the identified record.

At task 10-1120, a determination is made whether the user that is logged on (e.g., the HME provider) is permitted to modify the retrieved record. If the HME provider is already associated with the patient record by the physician or another entity, the HME provider is permitted to modify the retrieved record. The determination may be made, for example, based on (i) a permissions structure, such as the structure 350 and (ii) a log-in name (or another credential) used by the HME provider to log-in at task 910. If the HME provider is pre-authorized to modify the retrieved patient file, task 10-1140 may be executed. Otherwise the execution of the process 800 proceeds to task 10-1130, where the HME provider verifies the patient's identity to ensure that the retrieved record is for the same patient that is being treated by the physician.

At task 10-1130, it is determined whether the retrieved record belongs to the patient 120 (e.g., the patient that provided the removable storage medium 170 to a physician or a HME provider). Upon finding a match, modifying, by the server 200, the permissions structure associated with the retrieved patient record to permit the user associated with the HME provider terminal 150 to access, share, and/or modify the retrieved data object. If a match is not found, the user, is refused permission to modify the retrieved patient record, and the process 10-1100 terminates.

At task 10-1140, at least a part of the HME provider information record 152 may be automatically copied into the patient record. The copied information may include HME provider name, organization address, telephone number, or any other type of physician information that is normally kept in medical records. The information may be stored into the patient record by transmitting a query, over the network 160, from the HME provider terminal 150 to the server 200. Task 10-1140 may be executed only if the HME provider associated with the HME provider terminal 150 is permitted to modify the retrieved data structure.

FIG. 18A depicts a flowchart of a process 10-1200A associated with the verification of a patient's identity by a user, in accordance with one example of task 830 or 10-1130. The user may be a physician using the physician terminal 140 (step 830) or an HME provider using the HME provider terminal 150 (step 10-1130). The process 10-1200A may be performed to ensure that the record retrieved by the search performed at task 640 or 940 belongs to the user associated with the HME device 130 (e.g., the user or patient 120). Executing the process 10-1200A may prevent physicians or HME providers from modifying the wrong patient record in the records management system 110.

At task 10-1210A, one or more items of information are retrieved from the record retrieved at task 640 (or 940) and presented to the user. The items of information may include patient name, patient address, age, date of birth, social security number, or other similar information. At task 10-1220A, user input is received indicating whether the presented information belongs to the patient 120. For example, the information may be displayed on a display screen of a terminal together with a "Yes" and "No" buttons and the user may be permitted to click on one of those buttons to indicate whether the displayed information matches that of the patient 120. If the indication is positive, at task 10-1230A the user is granted permission to modify, access, or share the record retrieved at task 640 (or 940). In instances where the user has, logged in using an entity-wide credential, permission may be granted to the whole entity. Otherwise, if the user input indicates that the presented information does not belong to the patient 120, permission is denied at task 10-1240A.

FIG. 18B depicts a flowchart of a process 10-1200B associated with the verification of a patient's identity by a user, in accordance with another example of tasks 830 and 10-1130. In this example, the user is required to use an item of information about the patient 120 as a password. Furthermore, in this example, the user may be denied permission to view or otherwise access the record retrieved at task 640 (or 940) until the process 10-1200B is completed successfully. The process 10-1200B may be executed by one of the terminals 140 and 150, by the server 200, or by both the server 200 and one of the terminals 140-150.

At task 10-1210B, the user is required to provide a first item of information about the patient 120 (e.g., name, age, address, etc.) At task 10-1220B, an indication of the first item of information is received as user input. At task 10-1230B, a second item of information is obtained from the record obtained at task 640 (or 940). The second item of information may be of the same type as the first item. That is, if the first item is a patient name, then the second item may also be a patient name or if the first item is patient social security number, then the second item may also be asocial security number. At task 10-1240B, a determination is made whether the first item matches the second item of information. The two items of information are identical or otherwise satisfy a predetermined condition that specifies what it means for two information items to match. If the two items of information match, task 10-1250B is executed and the user is granted permission to modify, access, or share the record retrieved at task 640 (or 940). As discussed above, in instances where the user has logged in using an entity-wide credential, permission may be granted to the whole entity. Otherwise, if the two items do not match, permission is denied at task 10-1260B.

FIGS. 12-18B are provided as an example. At least some of the tasks associated with FIGS. 12-18B may be performed in a different order than represented, performed concurrently or altogether omitted. Furthermore, some or all of the tasks discussed with respect to processes 600 to 10-1100 may be combined together into a single embodiment. For instance, although in the above example three layers of authentication are used, namely at tasks 610/910, 630/930, and 830/10-1130, in other examples none or fewer of those authentication layers may be employed. For example, as indicated by the dashed lines of their respective blocks, the execution of tasks 630/930 may be optional. That is, in some instances, the process 600/900 may be executed without the removable storage medium 170 (or the HME device identifier 174 stored on the removable storage medium 170) being used for authentication purposes. In another example, the removable storage medium 170 or the HME device identifier stored on the removable storage medium 170 may be only informally used as an authentication mechanism. In such situations, the authentication discussed with respect to task 610/910 may have to be performed successfully in order for the user to be permitted to execute one or more of the remaining tasks or subtasks in the process 600/900. In yet another example, the authentication mechanism discussed with respect to tasks 830/10-1.130 may be the only authentication mechanism used.

In some instances, the determination whether a user should be permitted to execute one or more of the tasks associated with process 600/900, in accordance with any one of the authentication mechanisms discussed with respect to tasks 610/910, 630/930, and 830/10-1130, may be made by the records management system 110, in other instances the determination may be made on the client-device-end (e.g., by the terminal 140 or the terminal 150). It should be understood that, in some instances, at least some of the tasks or subtasks associated with the processes 600 and 900 may be executed using one of the processors 144 and 154. Moreover, in some instances, at least some of the tasks or subtasks associated with the processes 600 and 900 may be executed by the records management application 250.

Although in the above examples, tasks 710-750 are executed by making remote calls to the records management system 110 to include and modify the patient record 234, in other examples tasks 710-750, 810, 840, 10-1010-1050, 10-1110, and 10-1140 may executed by creating a record (e.g., a text file, database table, or another data structure) in local memory, modifying the record while it is still in local memory, and then uploading the record to the server 200. In that regard, the patient record 234 is not limited to being a database record, and rather it can be any other file or data structure capable of storing the information discussed above. The disclosure is not limited to any particular type of data record or method for modifying data records.

Although the portions 310-360 of the patient record 234 are depicted in FIG. 9 as integrated together in the same data structure, in other examples they may be independent data structures. Furthermore, in other examples, the patient record 234 may be a text file, or another type of file, that is not part of a relational database. In such instances, the executable code 240 may include any software for accessing or modifying that file. The disclosure is not limited to any particular implementation of the records storage aspects of the record management system.

Although in this example the server 200 is described as performing a plurality of functions by itself, in other examples the functions of the server 200 may be distributed among multiple servers that are part of the records management system 110. For example, the HTTP server discussed above may be executed on a different device (and not on the server 200). As another example, the database (or another similar system) that is used to store the patient records may also be implemented on a different device (and not on the server 200). To that end, although in the above examples the records management system 110 is depicted as including a single server, in other examples the records management system 110 may include multiple servers (dedicated to performing different functions), load balancers, network switches, or any other similar equipment that is normally associated with record management systems.

As these and other variations and combinations of the features discussed above can be utilized without departing from the subject matter as defined by the claims, the foregoing description of exemplary aspects should be taken by way of illustration rather than by way of limitation of the subject matter as defined by the claims. It will also be understood that the provision of the examples described herein (as well as clauses phrased as "such as," "e.g.", "including" and the like) should not be interpreted as limiting the claimed subject matter to the specific examples; rather, the examples are intended to illustrate only some of many possible aspects.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

4.7.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen, therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute: The casing of the centrifugal pump that receives the air being pumped by the impeller, slowing down the flow rate of air and increasing the pressure. The cross-section of the volute increases in area towards the discharge port.

4.7.3 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in liters per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

4.7.4 PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Noise, conducted: (how measured, typical values)

Noise, transmitted: (how measured, typical values)

Pressure: Force per unit area. Pressure may be measured in a range of units, including $cmH_2O$, $g\text{-}f/cm^2$, hectopascal. 1 $cmH_2O$ is equal to 1 $g\text{-}f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20\times10^{-6}$ pascal (Pa), considered the threshold of human hearing.

4.7.5 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

4.7.6 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.8 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to, the illustrative embodiments and that other arrangements may be devised without departing from the spirit and scope of the technology.

The invention claimed is:

1. A method for managing data associated with a home medical equipment (HME) device provided to a patient, the method comprising:
   receiving, by one or more processors, an HME device identifier associated with the HME device, the HME device identifier being a unique identifier, so as to avoid a duplicate to distinguish the HME device provided to the patient from other HME devices registered at a computer-based records management system;
   searching, by the one or more processors, the records management system for a patient record that is associated with the HME device identifier, the search being performed by using a search key unique to the HME device identifier;
   upon the search failing to retrieve any patient record associated with the HME device identifier, automatically generating, by the one or more processors, a new HME device associated patient record, wherein automatically generating the HME device associated patient record comprises:
   automatically incorporating patient information of the patient into the HME device associated patient record; and
   storing the HME device identifier into the HME device associated patient record, wherein the storing allows the patient information to be accessed via the HME device associated patient record in connection with an HME device identifier search.

2. The method of claim 1, wherein the HME device identifier associated with the HME device is received from a removable storage medium.

3. The method of claim 2, wherein the HME device identifier is engraved or encoded on an external surface of the removable storage medium.

4. The method of claim 1, further comprising, in response to the search successfully retrieving a patient record associated with the HME device identifier:
   facilitating, by the one or more processors, a verification of the patient's identity; and
   providing access and/or editing rights to an entity initiating the search by providing the HME device identifier.

5. The method of claim 4 further including, before providing access and/or editing rights to the entity, automatically associating the patient record with an entity providing the HME device identifier.

6. The method of claim 5, wherein the automatic association of the patient record with the entity providing the HME device identifier comprises receiving at least one of: an item of information associated with a physician and an item of information associated with an HME provider in charge of dispensing the HME device to the patient.

7. The method of claim 1, further comprising storing, in a computer memory and by the one or more processors, a physician identifier of a physician associated with the patient or an HME identifier of an HME associated with the patient, into the HME device associated patient record.

8. The method of claim 7, wherein the HME device identifier is a manufacturer's serial number.

9. A system for managing data associated with a home medical equipment (HME) device provided to a patient, the system comprising:
   a memory;
   a reader device configured to accept a removable storage medium including an HME device identifier, the HME device identifier being a unique identifier, so as to avoid a duplicate to distinguish the HME device provided to the patient from other HME devices registered at a computer based records management system; and one or more processors coupled to the memory and the reader device, the one or more processors being configured to:

retrieve the HME device identifier from the removable storage medium;

search the records management system for a patient record that is associated with the HME device identifier, the search being performed by using a search key unique to the HME device identifier;

upon the search failing to retrieve any patient record associated with the HME device identifier, automatically generate a new HME device associated patient record, wherein automatically generating the HME device associated patient record comprises:

automatically incorporating patient information of the patient into the HME device associated patient record; and storing the HME device identifier into the HME device associated patient record, wherein the storing allows the patient information to be accessed via the HME device associated patient record in connection with an HME device identifier search.

10. The system of claim 9, wherein the one or more processors is further configured, in response to the search successfully retrieving a record associated with the HME device identifier, to:

facilitate a verification of the patient's identity, and provide access and/or editing rights to an entity providing the HME device identifier.

11. The system of claim 10, wherein the one or more processors is further configured to automatically associate the patient's record with the entity providing the HME device identifier.

12. The system of claim 11, wherein the automatic association of the patient's record with the entity providing the HME device identifier comprises receiving at least one of: an item of information associated with a physician and an item of information associated with an HME provider in charge of dispensing the HME device to the patient.

13. The system of claim 9, wherein the one or more processors is further configured to store into the HME device associated patient record a physician identifier of a physician associated with the patient or an HME identifier of an HME associated with the patient, the storing being performed only when the removable storage medium is collocated with the system.

14. The system of claim 9, wherein the HME device identifier is a manufacturer's serial number.

* * * * *